(12) United States Patent
Kobayashi

(10) Patent No.: US 10,973,479 B2
(45) Date of Patent: Apr. 13, 2021

(54) X-RAY DIAGNOSIS APPARATUS, X-RAY DIAGNOSIS APPARATUS CONTROLLING METHOD, AND X-RAY DIAGNOSIS SYSTEM

(71) Applicant: Toshiba Medical Systems Corporation, Otawara (JP)

(72) Inventor: Yoshimasa Kobayashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 813 days.

(21) Appl. No.: 15/592,878

(22) Filed: May 11, 2017

(65) Prior Publication Data

US 2017/0325766 A1    Nov. 16, 2017

(30) Foreign Application Priority Data

May 16, 2016  (JP) .............................. JP2016-098094
May 8, 2017   (JP) .............................. JP2017-092388

(51) Int. Cl.
*A61B 6/00* (2006.01)
*A61B 6/02* (2006.01)

(52) U.S. Cl.
CPC .............. *A61B 6/487* (2013.01); *A61B 6/025* (2013.01); *A61B 6/5205* (2013.01)

(58) Field of Classification Search
CPC ...... A61B 6/025; A61B 6/0407; A61B 6/0457; A61B 6/465; A61B 6/487; A61B 6/5205
See application file for complete search history.

(56) References Cited

U.S. PATENT DOCUMENTS

2003/0118146 A1* 6/2003 Shida .................. A61B 6/032
378/4
2005/0105692 A1* 5/2005 Fadler .................. A61B 6/10
378/197

(Continued)

FOREIGN PATENT DOCUMENTS

JP          8-238232      9/1996
JP       2004-517070 A    6/2004

(Continued)

OTHER PUBLICATIONS

Japanese Office Action dated Mar. 2, 2021 issued in Japanese Application No. 2017-092388.

*Primary Examiner* — Chih-Cheng Kao
(74) *Attorney, Agent, or Firm* — Oblon, McClelland, Maier & Neustadt, L.L.P.

(57) ABSTRACT

According to one embodiment, an X-ray diagnosis apparatus includes an X-ray tube, an input interface, a holding mechanism, an X-ray detector, a display, and processing circuitry. The X-ray tube is configured to radiate X-rays. The input interface is configured to receive an input manual operation of designating at least a direction. The holding mechanism is configured to hold the X-ray tube, and to move the X-ray tube in accordance with the input manual operation, the X-ray tube radiating X-rays during the moving. The X-ray detector is configured to detect X-rays radiated from the X-ray tube and passing through an object, the X-ray detector generating X-ray image data based on the detected X-rays. The display is configured to subsequently display an X-ray image based on the X-ray image data.

11 Claims, 12 Drawing Sheets

(56) References Cited

U.S. PATENT DOCUMENTS

| | | | |
|---|---|---|---|
| 2005/0135558 A1* | 6/2005 | Claus | A61B 6/02 378/42 |
| 2009/0003679 A1 | 1/2009 | Ni et al. | |
| 2009/0123052 A1 | 5/2009 | Ruth et al. | |
| 2010/0172465 A1 | 7/2010 | Sawada et al. | |
| 2011/0075795 A1 | 3/2011 | Akahori | |
| 2014/0369464 A1* | 12/2014 | Lee | A61B 6/503 378/41 |
| 2015/0359501 A1* | 12/2015 | Eronen | A61B 6/032 378/62 |
| 2016/0120495 A1* | 5/2016 | Miyazawa | A61B 6/54 378/21 |
| 2017/0249758 A1* | 8/2017 | Mistretta | A61B 6/5223 |

FOREIGN PATENT DOCUMENTS

| | | |
|---|---|---|
| JP | 2009-11826 | 1/2009 |
| JP | 2010-158299 | 7/2010 |
| JP | 2011-67503 | 4/2011 |
| JP | 2014-128716 | 7/2014 |
| WO | WO 2014/174857 A1 | 10/2014 |

* cited by examiner

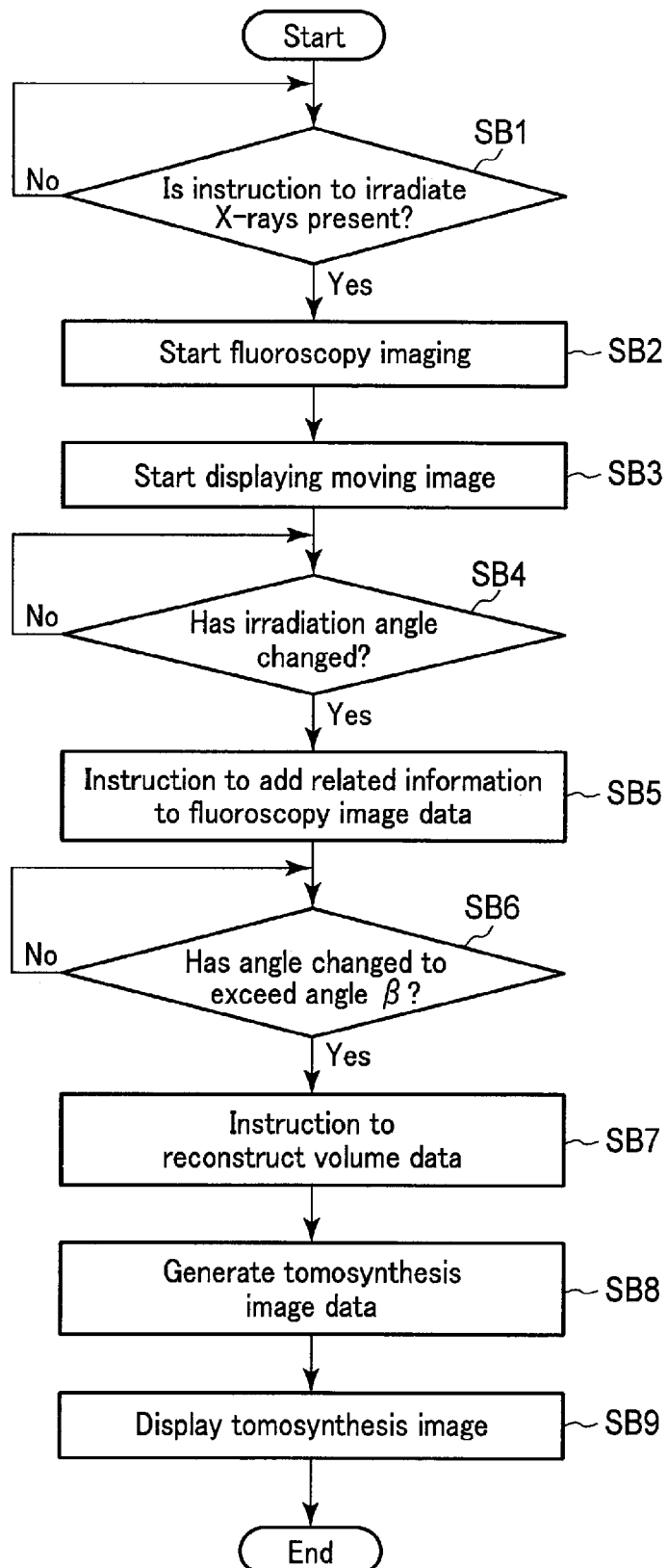
F I G. 5

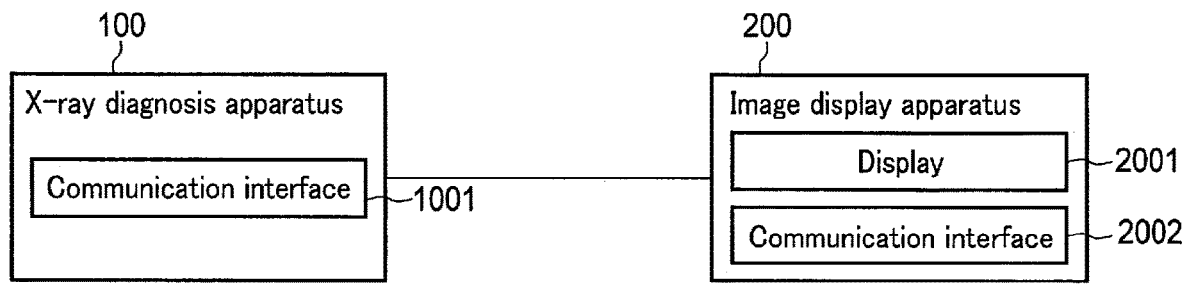
F I G. 12
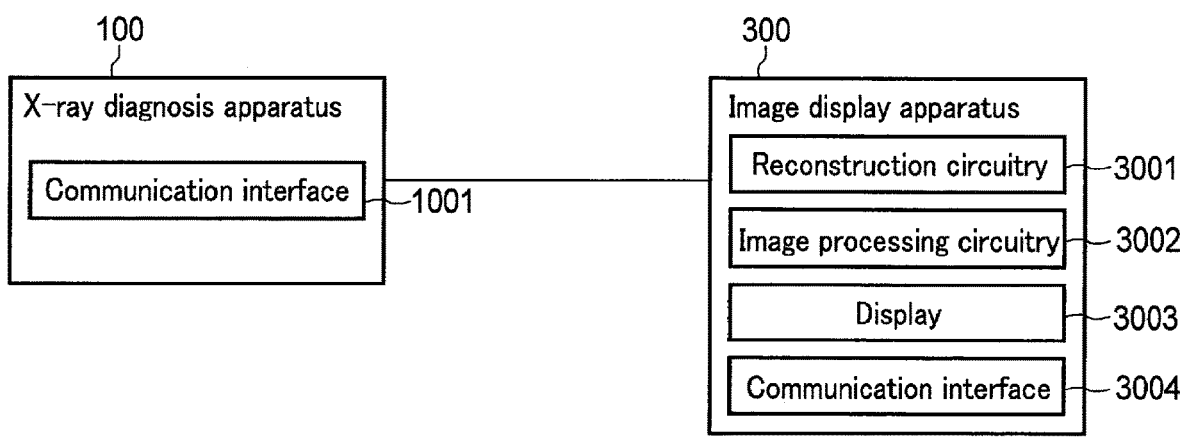
F I G. 13

X-RAY DIAGNOSIS APPARATUS, X-RAY DIAGNOSIS APPARATUS CONTROLLING METHOD, AND X-RAY DIAGNOSIS SYSTEM

CROSS-REFERENCE TO RELATED APPLICATIONS

This application is based upon and claims the benefit of priority from the prior Japanese Patent Application No. 2016-098094, filed May 16, 2016 and No. 2017-92388, filed May 8, 2017, the entire contents of both which are incorporated herein by reference.

FIELD

Embodiments described herein relate generally to an X-ray diagnosis apparatus, an X-ray diagnosis apparatus controlling method, and an X-ray diagnosis system.

BACKGROUND

In the field of mammography or X-ray TV systems, etc., tomosynthesis imaging is performed to reduce overlapping of tissue of a subject of imaging and problems due to structural noise. An image in which the overlapping of tissue of a subject of imaging and problems due structural noise are reduced can be obtained by performing tomosynthesis imaging, compared to a conventional two-dimensional image. Thus, it becomes possible to improve accuracy of diagnosis, to observe only a desired body part, and to fix a position of a catheter device.

Herein, as with ERCP (endoscopic retrograde cholangiopancreatography) or bronchial tubes endoscopy, etc., if a procedure of advancing a device while looking at a real-time moving image displayed by fluoroscopy is adopted, a radiographer would find it troublesome to input instructions to start tomosynthesis imaging into an apparatus each time when wanting to see a tomosynthesis image. Furthermore, if tomosynthesis imaging is performed, it is necessary to perform X-ray irradiation apart from X-ray irradiation necessary for fluoroscopy imaging.

BRIEF DESCRIPTION OF THE DRAWINGS

FIG. 5 is a drawing showing an example of a flowchart of an operation controlled by system controlling circuitry 28A according to Modification 1.

FIG. 12 is a block diagram showing the configuration of an X-ray image diagnosis apparatus according to another embodiment.

FIG. 13 is a block diagram showing the configuration of an X-ray image diagnosis apparatus according to another embodiment.

DETAILED DESCRIPTION

According to one embodiment, an X-ray diagnosis apparatus includes an X-ray tube, an input interface, a holding mechanism, an X-ray detector, a display, and processing circuitry. The X-ray tube is configured to radiate X-rays. The input interface is configured to receive an input manual operation of designating at least a direction. The holding mechanism is configured to hold the X-ray tube, and to move the X-ray tube in accordance with the input manual operation, the X-ray tube radiating X-rays during the moving. The X-ray detector is configured to detect X-rays radiated from the X-ray tube and passing through an object, the X-ray detector generating X-ray image data based on the detected X-rays. The display is configured to subsequently display an X-ray image based on the X-ray image data. The processing circuitry is configured to associate the X-ray image data with information including at least a position of the X-ray tube, the X-ray tube radiating X-rays to generate the X-ray image data at the position, and to reconstruct volume data by using a plurality of the X-ray image data and the information associated with each of the X-ray image data.

First Embodiment

In the following, an X-ray diagnosis apparatus according to the first embodiment will be described with reference to the drawings.

Figure 1:
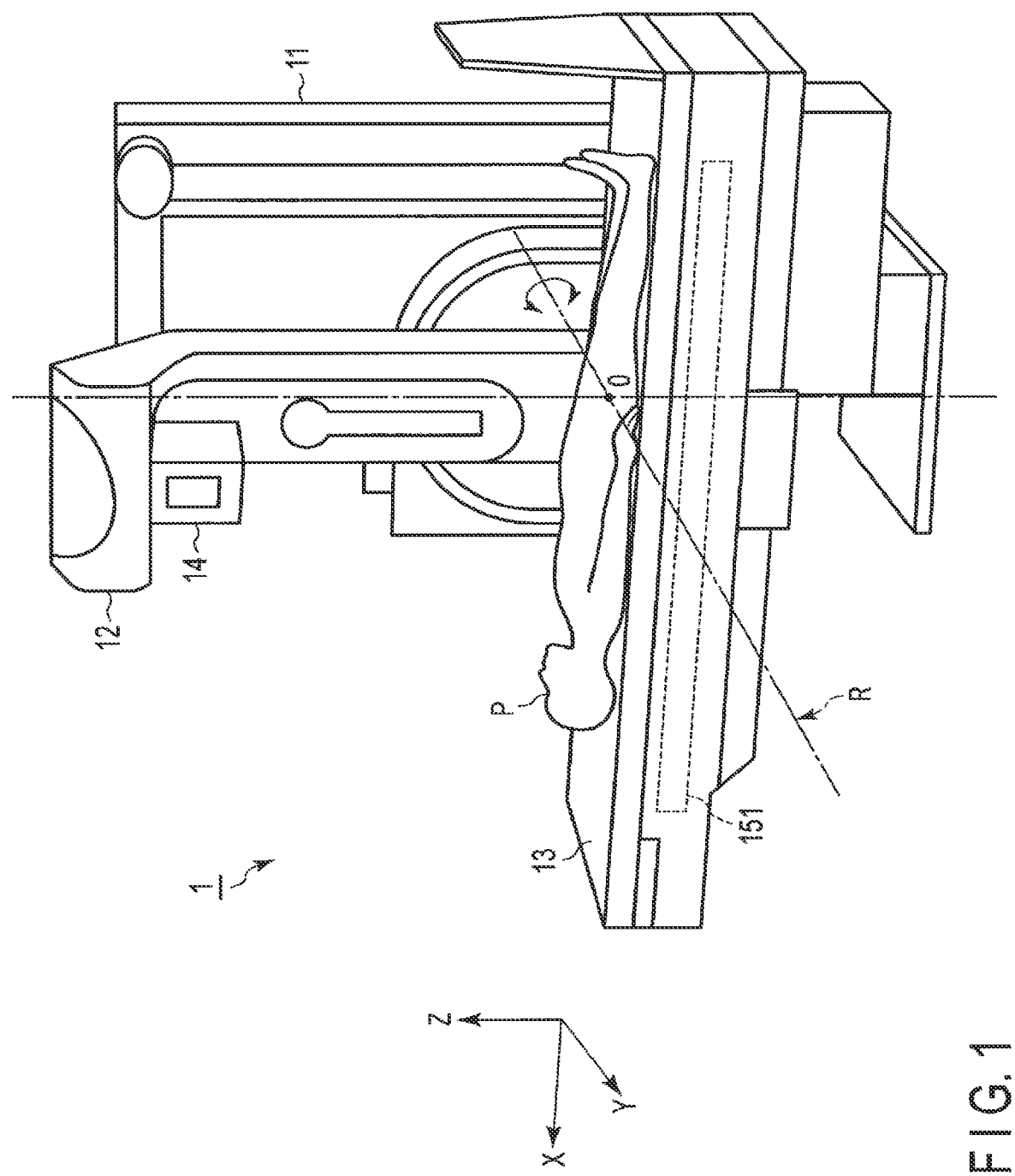
FIG. 1 is a drawing showing the outer appearance of an X-ray diagnosis apparatus according to a first embodiment.
Figure 2:
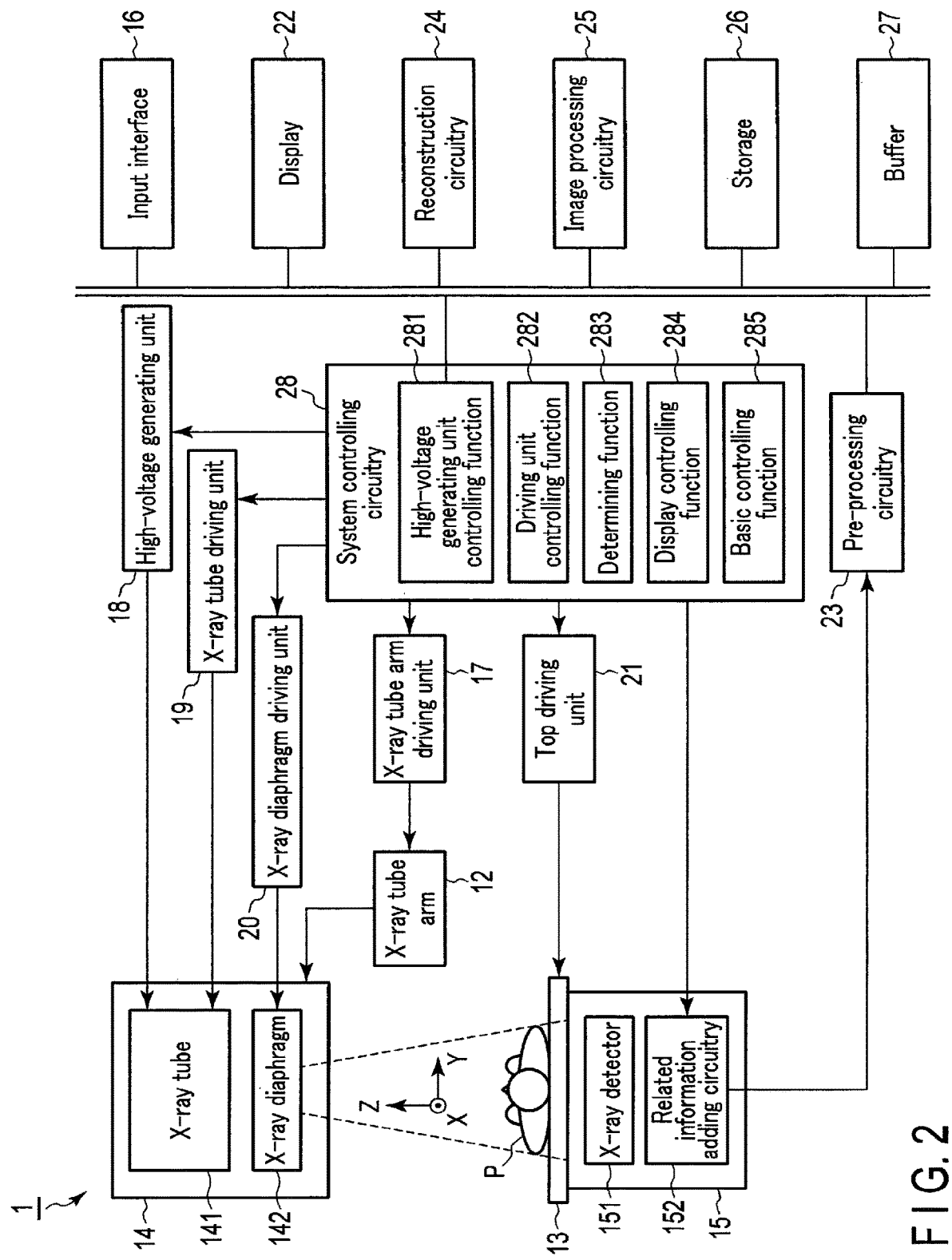
FIG. 2 is a block diagram showing the configuration of the X-ray image diagnosis apparatus according to the first embodiment.

FIG. 1 is a drawing showing the outer appearance of an X-ray diagnosis apparatus according to the first embodiment. FIG. 2 is a block diagram showing the configuration of the X-ray image diagnosis apparatus according to the first embodiment. The X-ray diagnosis apparatus 1 shown in FIG. 1 and FIG. 2 is, for example, an X-ray TV system. The X-ray diagnosis apparatus 1 according to the first embodiment is not limited to an X-ray TV system; it may be applicable to an X-ray diagnosis apparatus, such as a common X-ray imaging system, a blood vessel imaging system, an X-ray imaging system for doctor's rounds, a portable X-ray imaging apparatus, and the like, as appropriate. In the following, the first embodiment will be explained on the assumption that fluoroscopy imaging using an X-ray TV system is carried out. Fluoroscopy imaging is a technique of seeing through an object P by intermittently irradiating the object P with X-rays in accordance with a preset pulse width and exposure time to observe and examine the object P in a real-time manner on a TV monitor, etc.

As shown in FIG. 1, in the following description, the axis parallel with the body axis of the object P lying on the later-described top 13 is defined as the X-axis, the rotation central axis R is defined as the y-axis, and the Z-axis is defined perpendicular to the X-Y plane.

The X-ray diagnosis apparatus 1 has a support tube 11, an X-ray tube arm 12, a top 13, an X-ray output unit 14, and an X-ray detection unit 15, as shown in FIG. 1 and FIG. 2. The support tube 11 is connected to the X-ray tube arm 12 and the top 13. In this case, the X-ray tube arm 12 is supported in such a manner that the arm is allowed to move in a direction along the X-axis. The X-ray tube arm 12 is a holding mechanism that movably holds the X-ray output unit 14 in a predetermined rotation direction. Furthermore, the X-ray tube arm 12 is rotatably supported around the rotation central axis R which passes the support point O. The top 13 is movably supported in the direction along the X-, Y-, or Z-axis. The object P lies on the top 13.

The X-ray output unit 14 is provided at the end portion of the X-ray tube arm 12. The X-ray output unit 14 has an X-ray tube 141 and an X-ray diaphragm 142. The X-ray tube 141 generates X-rays, using a high voltage supplied from the later-described high-voltage generating unit 18. The X-ray tube 141 irradiates the object P lying on the top 13 with X-rays. The X-ray diaphragm 142 is arranged between the X-ray tube 141 and the top 13. The X-ray diaphragm 142 is attached to the irradiation hole portion of the X-ray tube 141. The X-ray diaphragm 142 is movable integrally with the X-ray tube 141 under the control of the later-described system controlling circuit 28. The X-ray diaphragm 142 has a plurality of diaphragm blades. The X-ray diaphragm 142 opens and closes the plurality of diaphragm blades under the control of the system controlling circuitry 28 to control the irradiation range of X-rays generated by the X-ray tube 141. An X-ray filter may be attached between the X-ray tube 141 and the X-ray diaphragm 142 in order to roughly equalize as needed the spatial radiation dosage distribution of X-rays incident to a later-described X-ray detector 151.

The X-ray detection unit 15 is provided on the back of the surface of the top 13 on which the object P lies. The X-ray detection unit 15 includes an X-ray detector 151 and related information adding (associating) circuitry 152. The X-ray detector 151 is an FPD (flat panel detector) for example. The X-ray detector 151 has a plurality of semiconductor detecting elements. A plurality of semiconductor detecting elements may be arranged in a two-dimensional lattice form, for example. The semiconductor detecting element may be of either a direct conversion type or an indirect conversion type. A direct conversion type is a scheme of directly converting incident X-rays into electric signals. An indirect conversion type is a scheme of converting incident X-rays into light by a fluorescent element and then converting the converted light into electric signals. The X-ray detector 151 detects X-rays that are generated from the X-ray tube 141 and pass through the object P, and converts the detected X-rays into electric signals. The X-ray detector 151 converts the converted electric signals into digital signals to generate fluoroscopy image data. The X-ray detector 151 outputs the generated fluoroscopy image data to the related information adding circuitry 152. As an X-ray detector 151, a photon-counting type detector may be used. As an X-ray detector 151, a combination of an image intensifier (I.I.) and a TV camera may be used.

The related information adding circuitry 152 is a processor for adding related information necessary to generate later-described volume data to the fluoroscopy image data that is output from the X-ray detector 151 in accordance with a control signal notified from the system controlling circuitry 28. The related information is imaging conditions, for example, an X-ray irradiation angle, an SID (source-image receptor distance), a field of view size, and X-ray conditions, etc. when the center of the effective surface of the X-ray detector 151 is irradiated with X-rays from the X-ray tube 141. The related information adding circuitry 152 invokes a built-in operation program, for example, and executes the invoked program to realize a function to be served by the related information adding circuitry 152.

When an instruction to add related information is received from the system controlling circuitry 28, the related information adding circuitry 152 adds corresponding related information to the fluoroscopy image data that is output from the X-ray detector 151. For example, the related information adding circuitry 152 adds related information for each frame unit to the fluoroscopy image data that is output immediately after receiving the instruction. The related information is supplied from, for example, the system controlling circuitry 28 to the related information adding circuitry 152. The related information adding circuitry 152 supplies later-described pre-processing circuitry 23 with the fluoroscopy image data to which the related information is added pre-processing. The related information adding circuitry 152 continues adding corresponding related information to fluoroscopy image data detected by the X-ray detector 151 until an instruction to stop adding related information is received after an instruction to add related information is received from the system controlling circuitry 28.

When an instruction to add related information is not received from the system controlling circuitry 28, the related information adding circuitry 152 does not add the related information to the fluoroscopy image data that is output from the X-ray detector 151, but supplies the pre-processing circuitry 23 with fluoroscopy image data to which related information is not added.

As shown in FIG. 2, the X-ray diagnosis apparatus 1 includes an input interface 16, an X-ray tube arm driving unit 17, a high-voltage generating unit 18, an X-ray tube driving unit 19, an X-ray diaphragm driving unit 20, a top driving unit 21, a display 22, pre-processing circuitry 23, reconstruction circuitry 24, image processing circuitry 25, a storage 26, and system controlling circuitry 28.

The input interface 16 has, for example, a mouse, a keyboard, a button, a panel switch, a touch command screen, a trackball, a joystick, etc. The input interface 16 has a foot switch for performing fluoroscopy imaging. The input interface 16 is connected to the system controlling circuitry 28 and acquires various instructions, commands, and information entered by a radiographer for the system controlling circuitry 28.

The X-ray tube arm driving unit 17 has a gear and a stepping motor, for example. The X-ray tube arm driving unit 17 is connected to the X-ray tube arm 12. The X-ray tube arm driving unit 17 has the X-ray tube arm 12 rotate about the rotation central axis R which passes the support point O, in accordance with location information of the X-ray tube arm 12 that is output from the system controlling circuitry 28. A plurality of fluoroscopy image data necessary to generate image data showing a desired cross section (hereinafter, referred to as tomosynthesis image data) can be obtained by performing fluoroscopy imaging by rotationally moving the X-ray tube arm 12.

The high-voltage generating unit 18 has an inverter circuit, for example. The high-voltage generating unit 18 is connected to the X-ray tube 141. The high-voltage generating unit 18 supplies the X-ray tube 141 with a voltage of a level designated by the system controlling circuitry 28.

The X-ray tube driving unit 19 has a gear and a stepping motor, for example. The X-ray tube driving unit 19 is connected to the X-ray tube 141 of the X-ray output unit 14. The X-ray tube driving unit 19 moves the X-ray tube 141 in the direction along the Y-axis, separately from the movement of the X-ray tube arm 12, in accordance with location information of the X-ray tube 141 that was instructed from the system controlling circuitry 28.

The X-ray diaphragm driving unit 20 has a gear and a stepping motor, for example. The X-ray diaphragm driving unit 20 is connected to the X-ray diaphragm 142 of the X-ray output unit 14. The X-ray diaphragm driving unit 20 opens and closes the plurality of diaphragm blades of the X-ray diaphragm 142, in accordance with an X-ray irradiation range instructed by the system controlling circuitry 28.

The top driving unit 21 has a gear and a stepping motor, for example. The top driving unit 21 is connected to the top 13. The top driving unit 21 moves the top 13 in the direction along the X-, Y-, or Z-axis, in accordance with location information of the top 13 that is output from the system controlling circuitry 28.

The display 22 has a display device such as a CRT display, a liquid crystal display, an organic EL display, a plasma display, etc. The display 22 displays a variety of information through, for example, the display device under the control of the system controlling circuitry 28. The display 22 displays, for example, pre-processed fluoroscopy image data generated by the later-described pre-processing circuitry 23, and tomosynthesis image data generated by the later-described image processing circuitry 25, under the control of the system controlling circuitry 28.

The pre-processing circuitry 23 is a processor that performs pre-processing on fluoroscopy image data supplied from the related information adding circuitry 152. The pre-processing circuitry 23 invokes an operation program from the later-described storage 26, for example, and executes the invoked program to realize a function to be served by the pre-processing circuitry 23. Pre-processing is, for example correction of sensitivity imbalance between pixels, and correction of omission (deficiency). The pre-processing circuitry 23 stores pre-processed fluoroscopy image data in a buffer 27, which will be described later. The pre-processing circuitry 23 may store preprocessed fluoroscopy image data in the storage 26.

The reconstruction circuitry 24 is a processor for reconstructing volume data based on a plurality of fluoroscopy image data to which related information is added, in accordance with control signals notified from the system controlling circuitry 28.

The reconstruction circuitry 24 invokes, for example, an operation program from the later-described storage 26 upon receiving an instruction to reconstruct volume data from the system controlling circuitry 28, and executes the invoked program to realize a function to be served as the reconstruction circuitry 24. The reconstruction circuitry 24 reads a plurality of fluoroscopy image data to which related information is added from the buffer 27. The reconstruction circuitry 24 reconstructs volume data for generating tomosynthesis image data based on a plurality of fluoroscopy image data to which related information is added. As a method of reconstructing volume data, a known tomography reconstruction method, such as a tomography reconstruction method based on a shift sum method, or a tomography reconstruction method based on an FBP (filtered back projection) method, etc., may be adopted.

The image processing circuitry 25 is a processor that generates tomosynthesis image data that is image data showing a desired cross-section, based on the volume data reconstructed by the reconstruction circuitry 24. A desired cross-section is a cross-section at a desired height in parallel with, for example, the X-Y plane. The image processing circuitry 25 invokes an operation program from the later-described storage 26, for example, and executes the invoked program to realize a function to be served by the image processing circuitry 25.

The storage 26 has a processor-readable storage medium, etc., like a magnetic or optical storage medium, or a semiconductor memory, etc. The storage 26 stores a program for realizing the function to be served by the pre-processing circuitry 23, the function to be served by the reconstruction circuitry 24, the function to be served by the image processing circuitry 25, the high-voltage generating unit controlling function 281, the driving unit controlling function 282, the determining function 283, the display controlling function 284, and the basic controlling function 285.

The buffer 27 has a processor-readable storage medium, etc., such as a magnetic or optical storage medium or a semiconductor memory, etc. The buffer 27 stores a predetermined number of fluoroscopy image data in, for example, a FIFO (first-in first-out) scheme. The buffer 27 may be provided in the storage 26.

The system controlling circuitry 28 is a processor for controlling each of the circuits constituting the X-ray diagnosis apparatus 1, for example. The system controlling circuitry 28 serves as the main component of the X-ray diagnosis apparatus 1. The system controlling circuitry 28 invokes each operation program from the storage 26, and executes the invoked program to realize the high-voltage generating unit controlling function 281, the driving unit controlling function 282, the determining function 283, the display controlling function 284, and the basic controlling function 285.

The high-voltage generating unit controlling function 281 is a function of controlling the high-voltage generating unit 18 in accordance with an instruction received from a radiographer via the input interface 16 to perform X-ray irradiation from the X-ray tube 141. Specifically, with the high-voltage generating unit controlling function 281 the system controlling circuitry 28 receives from, for example, the foot switch of the input interface 16, an instruction to perform X-ray irradiation. The system controlling circuitry 28 controls the high-voltage generating unit 18 when an instruction to perform X-ray irradiation is received, and intermittently radiates X-rays from the X-ray tube 141 to the object P in accordance with a preset pulse width and exposure time. Intermittent X-ray irradiation continues while, for example, the pedal of the foot switch is being stepped upon by the radiographer.

The driving unit controlling function 282 is a function of controlling the operation of each of the X-ray tube arm driving unit 17, the X-ray tube driving unit 19, the X-ray diaphragm driving unit 20, and the top driving unit 21 in accordance with the instruction received from the radiographer via the input interface 16, concurrently with the control of the intermittent X-ray irradiation by the high-voltage generating unit controlling function 281.

The determining function 283 is a function of making a determination in accordance with a change of a position of the X-ray tube 141 relative to the X-ray detector 151, and of making a predetermined instruction to the related information adding circuitry 152 and the reconstruction circuitry 24 based on a determination result. The relative change of a position is, for example, a change of an X-ray irradiation angle of the X-ray tube 141 with respect to the center of the effective surface of the X-ray detector 151 as a result of a rotational movement of the X-ray tube 141 concurrently with a rotational movement of the X-ray tube arm 12.

With the determining function 283, when it is determined that the change of the X-ray irradiation angle has begun, the system controlling circuitry 28 instructs the related information adding circuitry 152 to add corresponding related information to the fluoroscopy image data that is output from the X-ray detector 151. At this time, the system controlling circuitry 28 generates, based on imaging conditions during fluoroscopy imaging, related information corresponding to the fluoroscopy image data that are output from the X-ray detector 151. The system controlling circuitry 28 supplies the related information to the related information adding circuitry 152.

With the determining function 283, after the change of the X-ray irradiation angle has begun, when it is determined that the change of the X-ray irradiation angle is finished as the rotational movement of the X-ray tube arm 12 is stopped, the system controlling circuitry 28 instructs the reconstruction circuitry 24 to reconstruct volume data.

The display controlling function 284 is a function of having the display 22 display a plurality of fluoroscopy image data, or a plurality of fluoroscopy image data and tomosynthesis image data. Specifically, with the display controlling function 284, the system controlling circuitry 28 reads the plurality of fluoroscopy image data from the buffer 27. The system controlling circuitry 28 controls the display 22 to display the plurality of fluoroscopy image data as a moving image (fluoroscopy).

With the display controlling function 284, the system controlling circuitry 28 controls the image processing circuitry 25 to generate tomosynthesis image data based on the volume data generated by the reconstruction circuitry 24. The system controlling circuitry 28 controls the display 22 to display the generated tomosynthesis data as a tomosynthesis image. When display of the tomosynthesis image is displayed for a predetermined length of time, or when two-way display of a tomographic image may be repeated for a predetermined number of times, the display may be finished.

The basic controlling function 285 is a function of controlling basic operations, such as the input and output, etc. at the X-ray diagnosis apparatus 1. Specifically, with the basic controlling function 285, the system controlling circuitry 28 receives various instructions from the radiographer via the input interface 16. The system controlling circuitry 28 has the display 22 display an operation screen, etc. for the radiographer to operate.

Next, the operation of the first embodiment will be described. In the following description, suppose the operator manually operates the rotation movement of the X-ray tube arm 12 through the input interface 16, during fluoroscopy imaging. At this time, the operator designates at least a rotation direction of the X-ray tube arm 12. The operator may designate a rotation speed of the X-ray tube arm 12.

Figure 3:
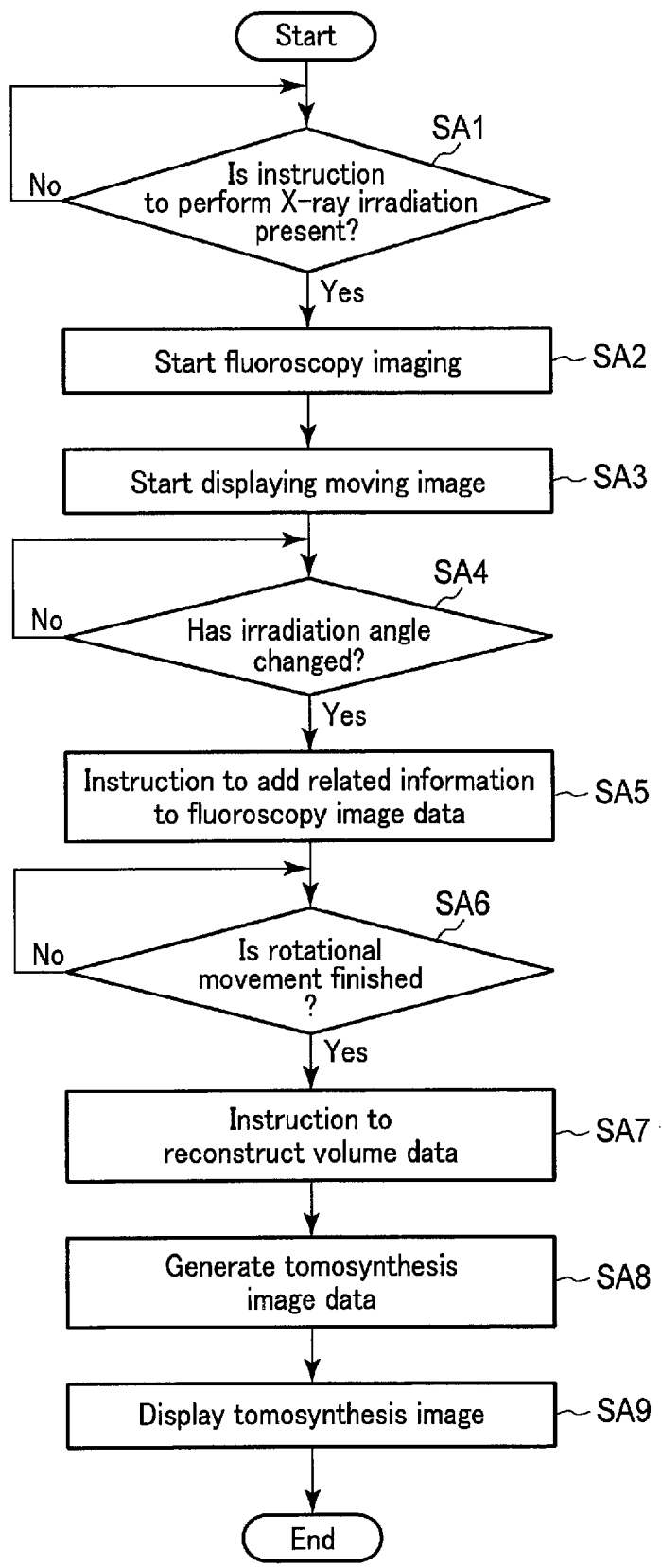
FIG. 3 is a drawing showing an example of a flowchart of an operation controlled by system controlling circuitry 28 according to the first embodiment.

FIG. 3 is a drawing showing an example of a flowchart of an operation controlled by the system controlling circuitry 28 according to the first embodiment.

As shown in FIG. 3, the system controlling circuitry 28 awaits until an instruction to perform X-ray irradiation is notified from the radiographer via the foot switch of the input interface 16 (step SA1).

The system controlling circuitry 28 controls the high-voltage generating unit 18 and the pre-processing circuitry 23 when an instruction to perform X-ray irradiation is notified from the radiographer ("Yes" in step SA1), and begins fluoroscopy imaging (step SA2).

The system controlling circuitry 28 controls the display 22 to display a moving image of a plurality of fluoroscopy image data (step SA3). The system controlling circuitry 28 receives an instruction from the radiographer via the input interface 16, and controls the operation of each unit during the fluoroscopy imaging.

The system controlling circuitry 28 determines, during the fluoroscopy imaging, whether a change of an X-ray irradiation angle that takes place as a result of the rotational movement of the X-ray tube arm 12 has begun or not (step SA4).

When it is determined that the change of the X-ray irradiation angle has begun ("Yes" in step SA4), the system controlling circuitry 28 instructs the related information adding circuitry 152 to add corresponding related information to the fluoroscopy image data that is output from the X-ray detector 151 (step SA5). At this time, the system controlling circuitry 28 generates, based on imaging conditions during fluoroscopy imaging, related information corresponding to the fluoroscopy image data that are output from the X-ray detector 151. The system controlling circuitry 28 supplies the related information to the related information adding circuitry 152. The system controlling circuitry 28 continues the generating and supplying until, for example, rotational movement of the X-ray tube 141 from the reference position is stopped, in other words, until the change of the X-ray irradiation angle is finished.

After the change of the X-ray irradiation angle has begun during fluoroscopy imaging, the system controlling circuitry 28 determines whether the change of the X-ray irradiation angle is stopped or not as a consequence of stopping the rotational movement of the X-ray tube arm 12 (step SA6).

When it is determined that the change of the X-ray irradiation angle has been finished ("Yes" in step SA6), the system controlling circuitry 28 instructs the reconstruction circuitry 24 to reconstruct volume data (step SA7). The reconstruction circuitry 24 reconstructs volume data using a plurality of fluoroscopy image data to which the related information is added, in accordance with an instruction from the system controlling circuitry 28.

The system controlling circuitry 28 controls the image processing circuitry 25 to generate tomosynthesis image data based on the volume data generated by the reconstruction circuitry 24 (step SA8).

The system controlling circuitry 28 controls the display 22 to display the generated tomosynthesis data as a tomosynthesis image (step SA9). At this time, the tomosynthesis image is displayed on the same monitor as the moving image of the plurality of fluoroscopy image data displayed in the step SA3.

According to the first embodiment, the system controlling circuitry 28 instructs the related information adding circuitry 152 to add corresponding related information to the fluoroscopy image data that is output from the X-ray detector 151, when the change of the relative position of the X-ray tube 141 with respect to the X-ray detector 151 i.e., the change of the X-ray irradiation angle, has begun during fluoroscopy imaging. After the change of the X-ray irradiation angle begins during fluoroscopy imaging, the system controlling circuitry 28 instructs the reconstruction circuitry 24 to reconstruct volume data using the plurality of fluoroscopy image data to which the related information is added when the change of the relative position of the X-ray tube 141 with respect to the X-ray detector 151, i.e., the change of the X-ray irradiation angle as a result of stopping the rotation movement of the X-ray tube arm 12, is finished. The system controlling circuitry 28 controls the image processing circuitry 25 to generate tomosynthesis image data based on the volume data generated by the reconstruction circuitry 24. The system controlling circuitry 28 controls the display 22 to display the generated tomosynthesis data as a tomosynthesis image. Thus, only by changing the relative position of the X-ray tube 141 with respect to the X-ray detector 151, it is possible to display the tomosynthesis image utilizing a plurality of related information-added fluoroscopy image data that are generated during tomography imaging.

Thus, according to the X-ray diagnosis apparatus 1 of the first embodiment, difficulties for a radiographer due to examination can be reduced, and X-ray exposure can also be reduced.

Modification 1

In the first embodiment, the system controlling circuitry 28 instructs the reconstruction circuitry 24 to reconstruct volume data when it is determined that the change of the X-ray irradiation angle has been finished. However, if it is desired to display a tomosynthesis image with higher accuracy, it becomes necessary to generate a plurality of fluoroscopy image data for a predetermined angle. Accordingly, in Modification 1, it will be described that system controlling circuitry instructs the reconstruction circuitry 24 to reconstruct volume data when it is determined that an X-ray irradiation angle is changed to exceed a predetermined angle. The outer appearance of the X-ray diagnosis apparatus 1A according to Modification 1 is the same as that in the first embodiment.

The X-ray diagnosis apparatus 1A has an input interface 16, an X-ray tube arm driving unit 17, a high-voltage generating unit 18, an X-ray tube driving unit 19, an X-ray diaphragm driving unit 20, a top driving unit 21, a display 22, pre-processing circuitry 23, reconstruction circuitry 24, image processing circuitry 25, a storage 26A, a buffer 27, and system controlling circuitry 28A.

The input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27 have the same configurations and functions as those of the input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27, shown in FIG. 2.

The storage 26A stores a predetermined rotation angle. A predetermined rotation angle is determined based on, for example, a preset pulse width and exposure time for X-ray irradiation, and a preset rotation speed of the X-ray tube arm 12, etc.

The system controlling circuitry 28A is a processor for controlling each of the circuits constituting the X-ray diagnosis apparatus 1A, for example. The system controlling circuitry 28A serves as the main component of the X-ray diagnosis apparatus LA. The system controlling circuitry 28A invokes each operation program from the storage 26A, and executes the invoked program to realize the high-voltage generating unit controlling function 281, the driving unit controlling function 282, the determining function 283A, the display controlling function 284, and the basic controlling function 285.

The determining function 283A is a function of making a determination in accordance with a change of a position of the X-ray tube 141 relative to the X-ray detector 151, and of making a predetermined instruction to the related information adding circuitry 152 and the reconstruction circuitry 24 based on a determination result. In the following, the determining function 283A will be specifically explained with reference to FIG. 4.

Figure 4:
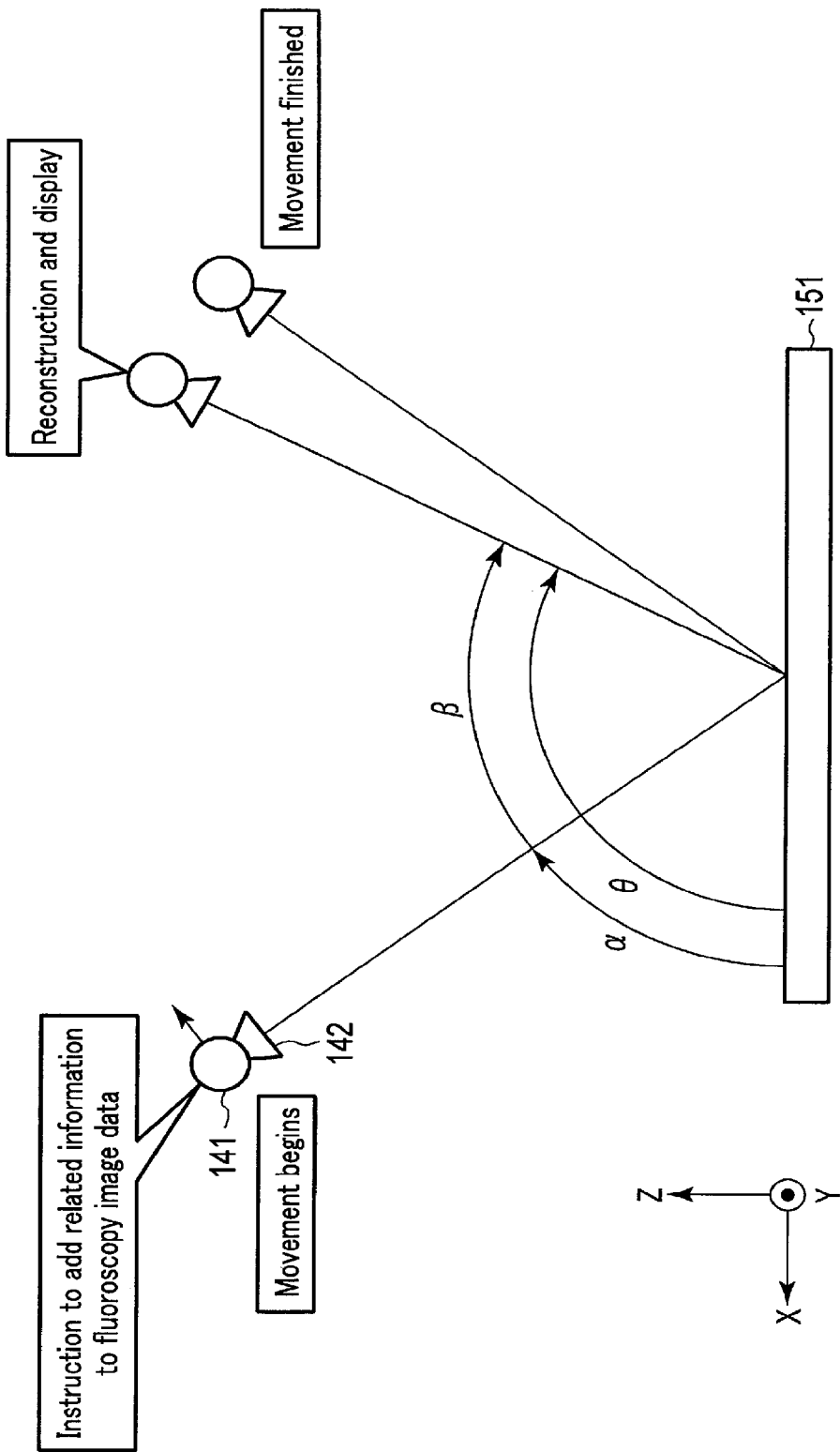
FIG. 4 is an explanatory drawing of an example of a predetermined rotation angle necessary to reconstruct volume data for displaying a desired tomosynthesis image according to Modification 1.

FIG. 4 is an explanatory drawing of an angle of a predetermined rotation angle necessary for volume data reconstruction to display a desired tomosynthesis image according to Modification 1. With the determining function 283A, as shown in FIG. 5, when the change of the X-ray irradiation angle begins, the system controlling circuitry 28A instructs the related information adding circuitry 152 to add corresponding related information to the fluoroscopy image data that is output from the X-ray detector 151.

The system controlling circuitry 28A stores, in the storage 26A, an X-ray irradiation angle α at the moment when the change of the X-ray irradiation angle begins, as shown in FIG. 4. The system controlling circuitry 28A calculates a rotation angle (θ-α) at a predetermined time interval, which is a difference between the X-ray irradiation angle θ after the change has begun and the X-ray irradiation angle α at the moment when the change of the X-ray irradiation angle begins. The system controlling circuitry 28A reads a predetermined rotation angle β from the storage 26A. The system controlling circuitry 28A compares the calculated rotation angle (θ-α) with the predetermined rotation angle β.

The system controlling circuitry 28A instructs the reconstruction circuitry 24 to reconstruct volume data when the calculated rotation angle (θ-α) exceeds the predetermined rotation angle β after the change of the X-ray irradiation angle has begun, as shown in FIG. 4. At this time, the reconstruction circuitry 24 reconstructs volume data using a plurality of fluoroscopy image data to which the related information corresponds to the angle β.

Next, the operation in Modification 1 will be described.

FIG. 5 is a drawing showing an example of a flowchart of an operation controlled by the system controlling circuitry 28A according to Modification 1. Steps SB1, SB2, SB3, SB4, SB5, SB7, SB8, and SB9 are respectively the same as steps SA1, SA2, SA3, SA4, SA5, SA7, SA8, and SA9 which are shown in FIG. 3. In the following, steps SB5, SB6, and SB7 will be described.

As shown in FIG. 5, when it is determined that the change of the X-ray irradiation angle begins ("Yes" in step SB4), the system controlling circuitry 28A instructs the related information adding circuitry 152 to add corresponding related information to the fluoroscopy image data that is output from the X-ray detector 151, (step SB5). At this time, the system controlling circuitry 28A generates, based on imaging conditions during fluoroscopy imaging, related information corresponding to the fluoroscopy image data that are output from the X-ray detector 151. The system controlling circuitry 28A supplies the related information to the related information adding circuitry 152. In step SB5, the system controlling circuitry 28A stores, in the storage 26A, the X-ray irradiation angle α at the time when the change of a X-ray irradiation angle begins. The system controlling circuitry 28A reads the predetermined rotation angle β from the storage 26A.

After the change of the X-ray irradiation angle begins during the fluoroscopy imaging, the system controlling circuitry 28A calculates, at a predetermined time interval, a rotation angle (θ-α) which is a difference between the X-ray irradiation angle θ after the change begins and the X-ray irradiation angle α at the moment when the change of the X-ray irradiation angle begins. The system controlling circuitry 28A compares the calculated rotation angle (θ-α) with the predetermined rotation angle β, and determines if the rotation angle (θ-α) exceeds the predetermined rotation angle β or not (step SB6).

When it is determined that the angle (θ-α) exceeds the angle β ("Yes" in step SB6), the system controlling circuitry 28A instructs the reconstruction circuitry 24 to reconstruct volume data (step SB7).

According to Modification 1, when it is determined that the calculated rotation angle (θ-α) exceeds the predetermined rotation angle β after the change of the X-ray irradiation angle has begun during fluoroscopy imaging, the system controlling circuitry 28A instructs the reconstruction circuitry 24 to reconstruct volume data. This enables display of a desired tomosynthesis image.

When the X-ray irradiation angle is changed more than the predetermined rotation angle β, the system controlling circuitry 28A may notify that the angle exceeds β via the display 22, for example.

If the X-ray tube 141 stops longer than a preset length of time during fluoroscopy imaging, the system controlling circuitry 28A sets the stop position as a reference position. When the X-ray tube 141 is rotationally moved more than the predetermined angle from the reference position, the system controlling circuitry 28A may instruct the reconstruction circuitry 24 to reconstruct volume data using the plurality of fluoroscopy image data to which the related information is added. At this time, even when the X-ray tube 141 is stopped after rotationally moving from the reference position for less than the predetermined angle, as long as the X-ray tube 141 starts rotationally moving again within a preset time, the system controlling circuitry 28A determines whether or not the X-ray irradiation angle, which is a sum of the rotation angles before and after the stop, is changed more than the predetermined rotation angle β.

Modification 2

In the first embodiment, the system controlling circuitry 28 instructs the reconstruction circuitry 24 to reconstruct volume data when it is determined that the change of the X-ray irradiation angle has been finished. In Modification 1, the system controlling circuitry 28A instructs the reconstruction circuitry 24 to reconstruct volume data when it is determined that an X-ray irradiation angle is changed to exceed a predetermined angle. In contrast, in Modification 2, it will be described that the reconstruction circuitry 24 is instructed to reconstruct volume data when the change of an X-ray irradiation angle is finished and it is determined that the X-ray irradiation angle is changed to exceed a predetermined angle. The outer appearance of the X-ray diagnosis apparatus 1B according to Modification 2 is the same as that in the first embodiment.

The X-ray diagnosis apparatus 1B includes an input interface 16, an X-ray tube arm driving unit 17, a high-voltage generating unit 18, an X-ray tube driving unit 19, an X-ray diaphragm driving unit 20, a top driving unit 21, a display 22, pre-processing circuitry 23, reconstruction circuitry 24, image processing circuitry 25, a storage 26B, a buffer 27, and system controlling circuitry 28B.

The input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27 have the same configurations and functions as those of the input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27, shown in FIG. 2.

The storage 26B has a configuration and a function similar to those of the storage 26A of Modification 1.

The system controlling circuitry 28B is a processor for controlling each of the circuits constituting the X-ray diagnosis apparatus 1B, for example. The system controlling circuitry 28B serves as the main component of the X-ray diagnosis apparatus 1B. The system controlling circuitry 28B invokes each operation program from the storage 26B, and executes the invoked program to realize the high-voltage generating unit controlling function 281, the driving unit controlling function 282, the determining function 283B, the display controlling function 284, and the basic controlling function 285.

The determining function 283B is a function of making a determination in accordance with a change of a position of the X-ray tube 141 relative to the X-ray detector 151, and of making a predetermined instruction to the related information adding circuitry 152 and the reconstruction circuitry 24 based on a determination result. Specifically, with the determining function 283B, when it is determined that the change of the X-ray irradiation angle has begun, the system controlling circuitry 28B instructs the related information adding circuitry 152 to add corresponding related information to the fluoroscopy image data that is output from the X-ray detector 151.

With the determining function 283B, the system controlling circuitry 28B stores, in the storage 26B, an X-ray irradiation angle α at the time when the change of the X-ray irradiation angle begins, as shown in FIG. 4. After the change of the X-ray irradiation angle has begun, when it is determined that the change of the X-ray irradiation angle is finished as a result of the stop of the rotational movement of the X-ray tube arm 12, the system controlling circuitry 28B calculates a rotation angle (θ-α) which is a difference between the X-ray irradiation angle θ at the time when the change of the X-ray irradiation angle is finished and the X-ray irradiation angle α at the moment when the change of the X-ray irradiation angle begins, as shown in FIG. 4. The system controlling circuitry 28B reads a predetermined rotation angle β from the storage 26B. The system controlling circuitry 28B compares the calculated rotation angle (θ-α) with the predetermined rotation angle β, and instructs the reconstruction circuitry 24 to reconstruct volume data when it is determined that (θ-α) exceeds β. When it is determined that (θ-α) is less than β, the system controlling circuitry 28B finishes the processing, for example. When it is determined that (θ-α) is less than β, the system controlling circuitry 28B may wait for a predetermined length of time until the change of the X-ray irradiation angle begins again.

Next, the operation in Modification 2 will be described.

Figure 6:
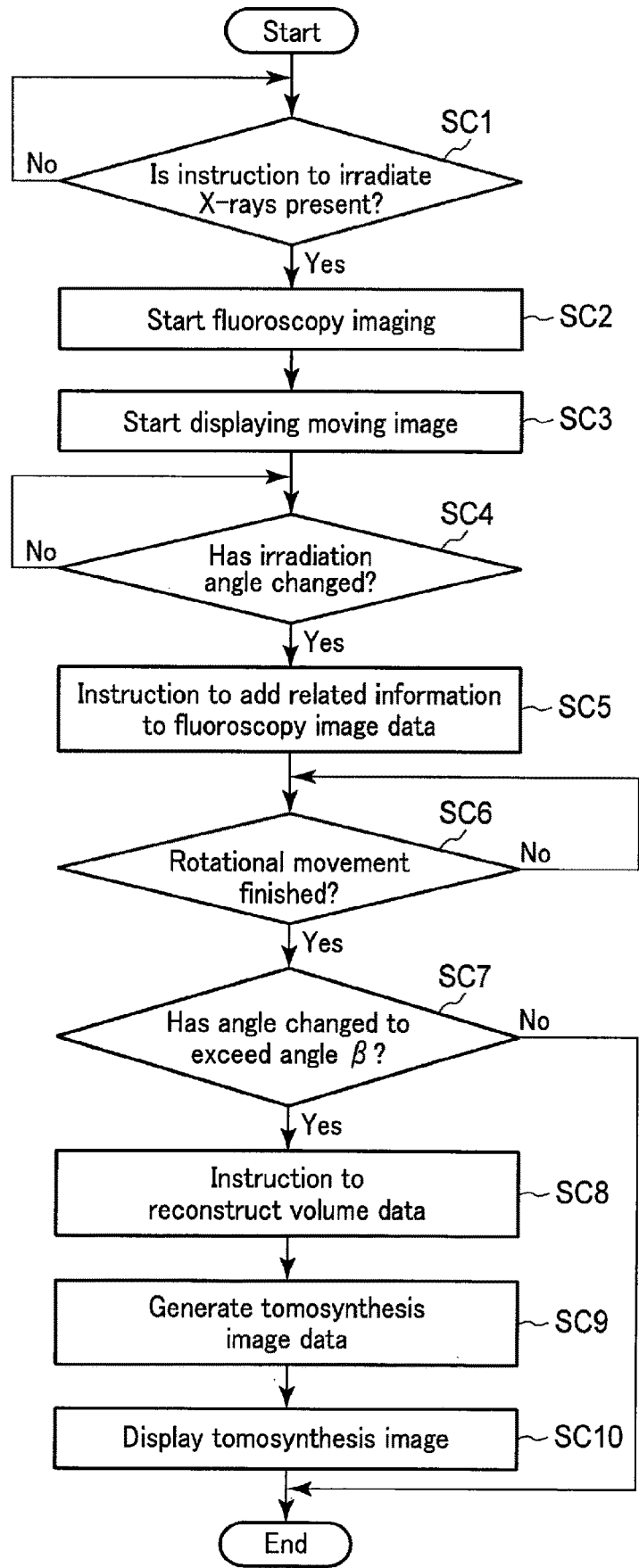
FIG. 6 is a drawing showing an example of a flowchart of an operation controlled by system controlling circuitry 28B according to Modification 2.

FIG. 6 is a drawing showing an example of a flowchart of an operation controlled by the system controlling circuitry 28B according to Modification 2. Steps SC1, SC2, SC3, SC4, SC5, SC7, SC8, SC9, and SC10 are respectively the same as steps SA1, SA2, SA3, SA4, SA5, SA6, SA7, SA8, and SA9 which are shown in FIG. 3. In the following, steps SC5, SC6, SC7, and SC8 will be described.

As shown in FIG. 6, when it is determined that the change of the X-ray irradiation angle has begun ("Yes" in step SC4), the system controlling circuitry 28B instructs the related information adding circuitry 152 to add corresponding related information to the fluoroscopy image data that is output from the X-ray detector 151 (step SC5). At this time, the system controlling circuitry 28B generates, based on imaging conditions during fluoroscopy imaging, related information corresponding to the fluoroscopy image data that are output from the X-ray detector 151. The system controlling circuitry 28B supplies the related information to the related information adding circuitry 152. In step SC5, the system controlling circuitry 28B stores, in the storage 26B, the X-ray irradiation angle $\alpha$ at the time when the change of the X-ray irradiation angle begins.

After the change of the X-ray irradiation angle has begun during fluoroscopy imaging, the system controlling circuitry 28B determines whether or not the change of the X-ray irradiation angle is stopped as a consequence of the stop of the rotational movement of the X-ray tube arm 12 (step SC6).

After the change of the X-ray irradiation angle has begun during fluoroscopy imaging, when it is determined that the change of the X-ray irradiation angle is finished ("Yes" in step SC6), the system controlling circuitry 28B reads the predetermined rotation angle $\beta$ from the storage 26B. The system controlling circuitry 28B calculates a rotation angle $(\theta-\alpha)$ which is a difference between the X-ray irradiation angle $\theta$ at the time when the change of the X-ray irradiation angle is finished and the X-ray irradiation angle $\alpha$ at the time when the change of the X-ray irradiation angle begins. The system controlling circuitry 28B compares the calculated rotation angle $(\theta-\alpha)$ with the predetermined rotation angle $\beta$, and determines whether or not the rotation angle $(\theta-\alpha)$ exceeds the predetermined rotation angle $\beta$ (step SC7).

When it is determined that $(\theta-\alpha)$ exceeds than $\beta$ ("Yes" in step SC7), the system controlling circuitry 28B instructs the reconstruction circuitry 24 to reconstruct volume data (step SC8). The system controlling circuitry 28B stops the processing when it is determined that the angle $(\theta-\alpha)$ is less than the angle $\beta$ ("No" in step SC7).

According to Modification 2, the system controlling circuitry 28B instructs the reconstruction circuitry 24 to reconstruct volume data when the change of the X-ray irradiation angle is finished during fluoroscopy imaging and it is determined that the rotation angle $(\theta-\alpha)$ exceeds than the predetermined rotation angle $\beta$. This enables the system controlling circuitry 28B to display a tomosynthesis image with higher accuracy.

Modification 3

In the first embodiment, the system controlling circuitry 28 instructs the reconstruction circuitry 24 to reconstruct volume data when it is determined that the change of the X-ray irradiation angle is finished. In Modification 1, the system controlling circuitry 28A instructs the reconstruction circuitry 24 to reconstruct volume data when it is determined that a rotation angle $(\theta-\alpha)$ exceeds than a predetermined rotation angle $\beta$. In Modification 2, the system controlling circuitry 28B instructs the reconstruction circuitry 24 to reconstruct volume data when the change of an X-ray irradiation angle is finished and it is determined that a rotation angle $(\theta-\alpha)$ exceeds than a rotation angle $\beta$. In contrast, in Modification 3, it will be described that a system controlling circuit instructs the reconstruction circuitry 24 to reconstruct volume data when the number of the related information-added fluoroscopy image data stored in the buffer 27 exceeds a predetermined number. The outer appearance of the X-ray diagnosis apparatus 1C according to Modification 3 is the same as that in the first embodiment.

The X-ray diagnosis apparatus 1C includes an input interface 16, an X-ray tube arm driving unit 17, a high-voltage generating unit 18, an X-ray tube driving unit 19, an X-ray diaphragm driving unit 20, a top driving unit 21, a display 22, pre-processing circuitry 23, reconstruction circuitry 24, image processing circuitry 25, a storage 26C, a buffer 27, and system controlling circuitry 28C.

The input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27 have the same configurations and functions as those of the input interface 16, the X-ray tube arm driving unit 17, the high-voltage generating unit 18, the X-ray tube driving unit 19, the X-ray diaphragm driving unit 20, the top driving unit 21, the display 22, the pre-processing 23, the reconstruction circuitry 24, the image processing circuitry 25, and the buffer 27, shown in FIG. 2.

The storage 26C stores a predetermined threshold N as a condition for performing volume data reconstruction and tomosynthesis image display. The threshold N is a value indicating a threshold of the number of frames of the related information-added fluoroscopy image data. The threshold N is determined based on, for example, a preset rotation speed of the X-ray tube arm 12 and a preset rotation angle necessary to display a tomosynthesis image with high accuracy.

The system controlling circuitry 28C is a processor for controlling each of the circuits constituting the X-ray diagnosis apparatus 1C, for example. The system controlling circuitry 28C serves as the main component of the X-ray diagnosis apparatus 1C. The system controlling circuitry 28C invokes each operation program from the storage 26C, and executes the invoked program to realize the high-voltage generating unit controlling function 281, the driving unit controlling function 282, the determining function 283C, the display controlling function 284, and the basic controlling function 285.

The determining function 283C is a function of making a determination in accordance with a change of a position of the X-ray tube 141 relative to the X-ray detector 151, and of making a predetermined instruction to the related information adding circuitry 152 based on a determination result. With the determining function 283C, when it is determined that the change of the X-ray irradiation angle has begun, the system controlling circuitry 28C instructs the related information adding circuitry 152 to add corresponding related information to the fluoroscopy image data that is output from the X-ray detector 151.

The determining function 283C is a function of instructing the reconstruction circuitry 24, after the change of the X-ray irradiation angle has begun, to reconstruct volume data when the number of the related information-added fluoroscopy image data stored in the buffer 27 exceeds the predetermined number.

In the following, an example of performing volume data reconstruction in response to an instruction from the determining function 283C will be specifically explained with reference to FIG. 7.

Figure 7:
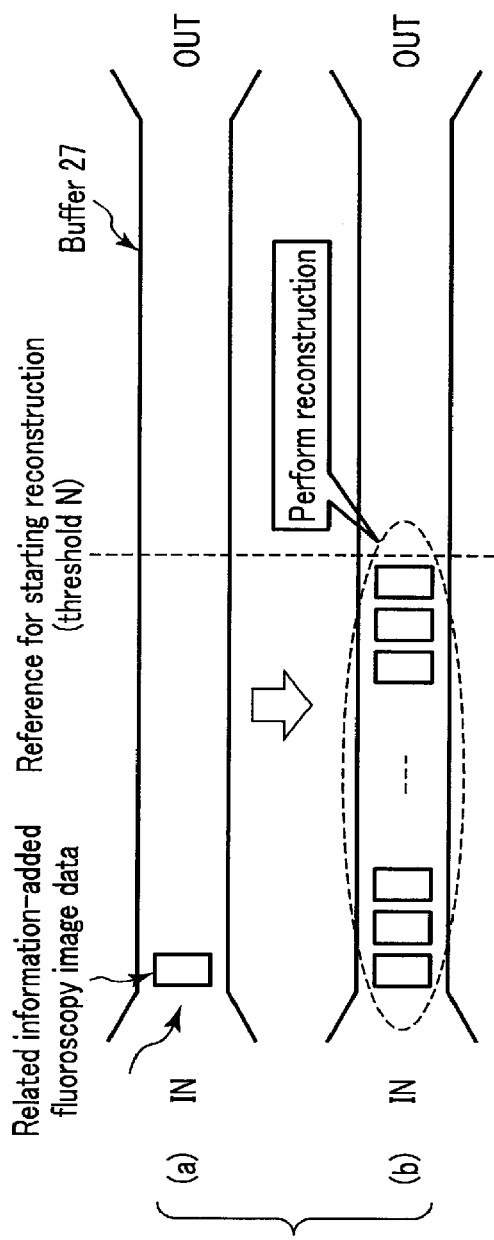
FIG. 7 is an explanatory drawing of an example of timing of instructing reconstruction circuitry 24 to reconstruct volume data according to Modification 3.

FIG. 7 is an explanatory drawing of an example of timing of instructing the reconstruction circuitry 24 to reconstruct volume data according to Modification 3. Hereinafter, for the sake of brevity, related information is presumed to be added to all the fluoroscopy image data stored in the buffer 27. As shown in FIG. 7, after the change of the X-ray irradiation angle has begun during fluoroscopy imaging, the system controlling circuitry 28C starts monitoring the number of related information-added fluoroscopy image data that is stored in the buffer 27 immediately after the change. The system controlling circuitry 28C compares the number of related information-added fluoroscopy image data that is stored in the buffer 27 immediately after the change with the threshold N at a predetermined time interval. If the number of the related information-added fluoroscopy image data is less than the threshold N, the system controlling circuitry 28C does not instruct the reconstruction circuitry 24 to reconstruct volume data, as shown in FIG. 7 (a). If the number of the fluoroscopy image data to which related information is added exceeds the threshold N, the system controlling circuitry 28C instructs the reconstruction circuitry 24 to reconstruct volume data, as shown in FIG. 7 (b).

Next, the operation in Modification 3 will be described.

Figure 8:
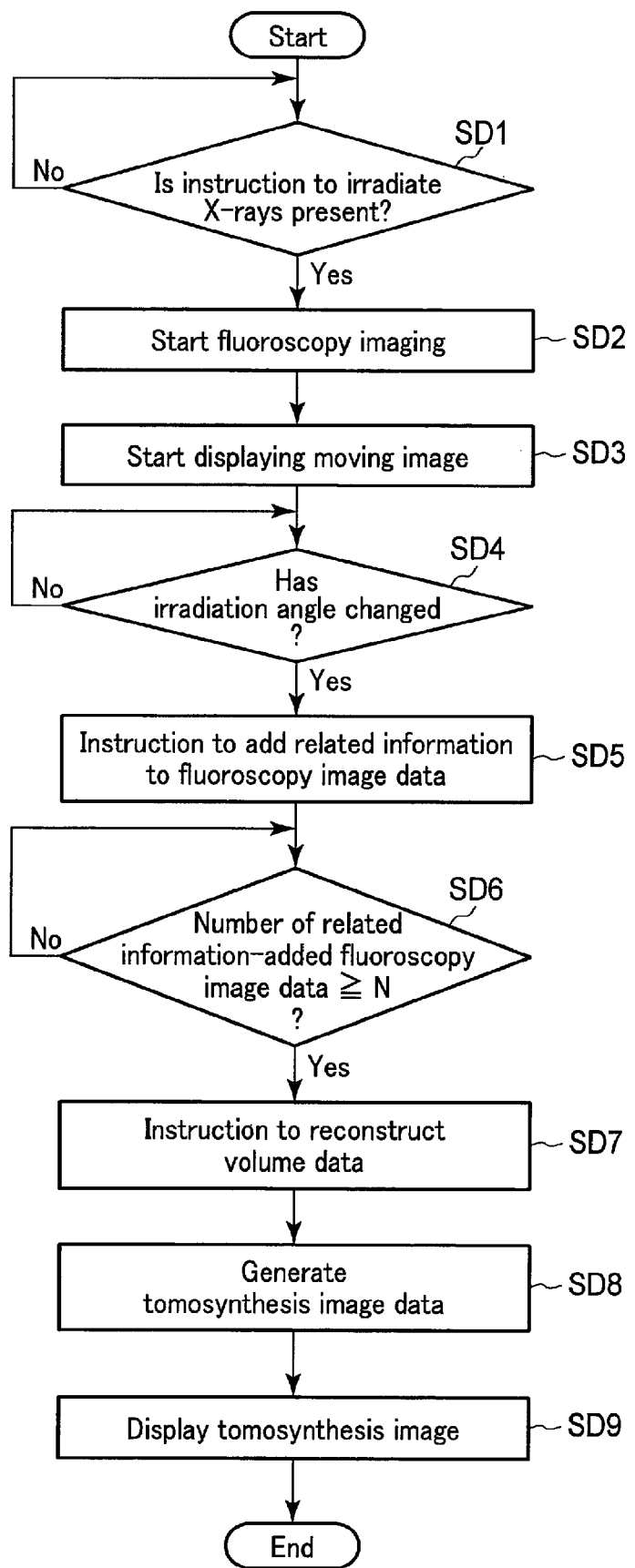
FIG. 8 is a drawing showing an example of a flowchart of an operation controlled by system controlling circuitry 28C according to Modification 3.

FIG. 8 is a drawing showing an example of a flowchart of an operation controlled by the system controlling circuitry 28C according to Modification 3. Steps SD1, SD2, SD3, SD4, SD5, SD7, SD8, and SD9 are respectively the same as steps SA1, SA2, SA3, SA4, SA5, SA7, SA8, and SA9 which are shown in FIG. 3. In the following, steps SD5, SD6, and SD7 will be described.

As shown in FIG. 8, when it is determined that the change of the X-ray irradiation angle begins ("Yes" in step SD4), the system controlling circuitry 28C instructs the related information adding circuitry 152 to add corresponding related information to the fluoroscopy image data that is output from the X-ray detector 151 (step SD5). At this time, the system controlling circuitry 28C generates, based on imaging conditions during fluoroscopy imaging, related information corresponding to the fluoroscopy image data that are output from the X-ray detector 151. The system controlling circuitry 28C supplies the related information to the related information adding circuitry 152. In step SD5, the system controlling circuitry 28C reads a predetermined threshold N from the storage 26C.

After the change of the X-ray irradiation angle has begun during fluoroscopy imaging, the system controlling circuitry 28C determines whether or not the number of related information-added fluoroscopy image data stored in the buffer 27 exceeds the threshold N at a predetermined time interval (step SC5).

When it is determined that the number of related information-added fluoroscopy image data stored in the buffer 27 exceeds the threshold N ("Yes" in step SD6), the system controlling circuitry 28C instructs the reconstruction circuitry 24 to reconstruct volume data using the related information-added fluoroscopy image data stored in the buffer (step SD7).

According to Modification 3, when it is determined that the number of related information-added fluoroscopy image data stored in the buffer 27 exceeds the threshold N, the system controlling circuitry 28C instructs the reconstruction circuitry 24 to reconstruct volume data. This enables the display of a tomosynthesis image with high accuracy.

If the X-ray tube 141 stops longer than a preset length of time during fluoroscopy imaging, the system controlling circuitry 28C sets the stop position as a reference position. The system controlling circuitry 28C may be configured to monitor the number of fluoroscopy image data to which related information corresponding to the X-ray irradiation from the reference position is added. For example, at this time, when the X-ray tube 141 is stopped for a time longer than a predetermined length of time while the number of fluoroscopy image data as a target for monitoring is less than N, the system controlling circuitry 28C deletes all the related information-added fluoroscopy image data stored in the buffer 27.

Modification 4

In Modification 3, the system controlling circuitry 28C instructs the reconstruction circuitry 24 to reconstruct volume data when the number of related information-added fluoroscopy image data stored in the buffer 27 exceeds a predetermined number. In Modification 4, it will be described that a system controlling circuit instructs the reconstruction circuitry 24 to reconstruct volume data when the change of an X-ray irradiation angle is finished and the number of related information-added fluoroscopy image data stored in the buffer 27 exceeds a predetermined threshold. The outer appearance of the X-ray diagnosis apparatus 1D according to Modification 4 is the same as that in the first embodiment.

The X-ray diagnosis apparatus 1D includes an input interface 16, an X-ray tube arm driving unit 17, a high-voltage generating unit 18, an X-ray tube driving unit 19, an X-ray diaphragm driving unit 20, a top driving unit 21, a display 22, pre-processing circuitry 23, reconstruction circuitry 24, image processing circuitry 25, a storage 26D, a buffer 27, and system controlling circuitry 28D.

The input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27 have the same configurations and functions as those of the input interface 16, the X-ray tube arm driving unit 17, the high-voltage generating unit 18, the X-ray tube driving unit 19, the X-ray diaphragm driving unit 20, the top driving unit 21, the display 22, the pre-processing circuitry 23, the reconstruction circuitry 24, the image processing circuitry 25, and the buffer 27, shown in FIG. 2.

The storage 26D has a configuration and a function similar to those of the storage 26C of Modification 3.

The system controlling circuitry 28D is a processor for controlling each of the circuits constituting the X-ray diagnosis apparatus 1D, for example. The system controlling circuitry 28D serves as the main component of the X-ray diagnosis apparatus 1D. The system controlling circuitry 28D invokes each operation program from the storage 26D, and executes the invoked program to realize the high-voltage generating unit controlling function 281, the driving unit controlling function 282, the determining function 283D, the display controlling function 284, and the basic controlling function 285.

The determining function 283D is a function of making a determination in accordance with a change of a position of the X-ray tube 141 relative to the X-ray detector 151, and of making a predetermined instruction to the related information adding circuitry 152 based on a determination result. With the determining function 283D, when it is determined that the change of the X-ray irradiation angle has begun, the system controlling circuitry 28D instructs the related information adding circuitry 152 to add corresponding related information to the fluoroscopy image data that is output from the X-ray detector 151.

The determining function 283D is a function of instructing the reconstruction circuitry 24 to reconstruct volume data after the change of the X-ray irradiation angle has begun, when the change of the X-ray irradiation angle is finished and the number of the related information-added fluoroscopy image data stored in the buffer 27 exceeds the predetermined number. Specifically, with the determining function 283D, after the change of the X-ray irradiation angle has begun during fluoroscopy imaging, the system controlling circuitry 28D starts monitoring the number of related information-added fluoroscopy image data that is stored in the buffer 27 immediately after the change, as shown in FIG. 7. The system controlling circuitry 28D compares the number of related information-added fluoroscopy image data that is stored in the buffer 27 immediately after the change with the threshold N at a predetermined time interval. When the change of the X-ray irradiation angle is finished and the number of related information-added fluoroscopy image data is less than the threshold N, the system controlling circuitry 28D does not instruct the reconstruction circuitry 24 to reconstruct volume data, as shown in FIG. 7 (a). When the change of the X-ray irradiation angle is finished and the number of related information-added fluoroscopy image data exceeds the threshold N, the system controlling circuitry 28D instructs the reconstruction circuitry 24 to reconstruct volume data, as shown in FIG. 7 (b).

Next, the operation in Modification 4 will be described.

Figure 9:
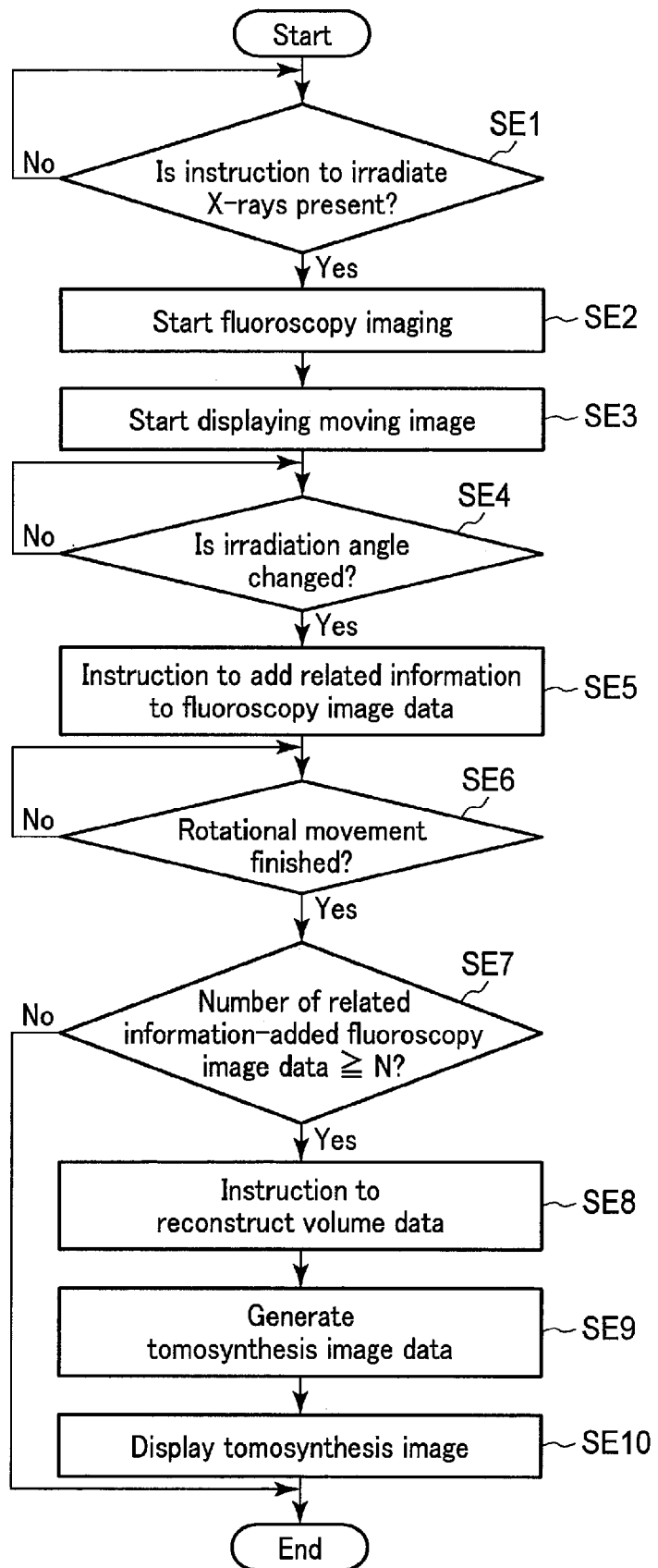
FIG. 9 is a drawing showing an example of a flowchart of an operation controlled by system controlling circuitry 28D according to Modification 4.

FIG. 9 is a drawing showing an example of a flowchart of an operation controlled by the system controlling circuitry 28D according to Modification 4. Steps SE1, SE2, SE3, SE4, SE5, SE7, SE8, SE9, and SE10 are respectively the same as steps SA1, SA2, SA3, SA4, SA5, SA6, SA7, SA8 and SA9 which are shown in FIG. 3. In the following, steps SE5, SE6, SE7, and SE8 will be described.

As shown in FIG. 9, when it is determined that the change of the X-ray irradiation angle has begun ("Yes" in step SE4), the system controlling circuitry 28D instructs the related information adding circuitry 152 to add related corresponding information to the fluoroscopy image data that is output from the X-ray detector 151 (step SE5). At this time, the system controlling circuitry 28D generates, based on imaging conditions during fluoroscopy imaging, related information corresponding to the fluoroscopy image data that are output from the X-ray detector 151. The system controlling circuitry 28D supplies the related information to the related information adding circuitry 152.

After the change of the X-ray irradiation angle has begun during fluoroscopy imaging, the system controlling circuitry 28D determines whether or not the change of the X-ray irradiation angle is stopped as a consequence of the stop of the rotational movement of the X-ray tube arm 12 (step SE6).

After the change of the X-ray irradiation angle has begun during fluoroscopy imaging, when it is determined that the change of the X-ray irradiation angle is finished ("Yes" in step SE6), the system controlling circuitry 28D reads the predetermined threshold N from the storage 26D. The system controlling circuitry 28D determines whether or not the number of related information-added fluoroscopy image data stored in the buffer 27 exceeds the threshold N (step SE7).

When it is determined that the number of related information-added fluoroscopy image data stored in the buffer 27 exceeds the threshold N ("Yes" in step SE7), the system controlling circuitry 28D instructs the reconstruction circuitry 24 to reconstruct volume data using the related information-added fluoroscopy image data stored in the buffer 27 (step SE8).

According to Modification 4, when the change of the X-ray irradiation angle is finished and it is determined that the number of related information-added fluoroscopy image data stored in the buffer 27 exceeds the predetermined threshold, the system controlling circuitry 28D instructs the reconstruction circuitry 24 to reconstruct volume data. This enables display of a tomosynthesis image with high accuracy.

Other Embodiments

The present invention is not limited to the foregoing embodiments. For example, when it is determined that the calculated rotation angle (θ-α) exceeds the predetermined rotation angle β after the change of the X-ray irradiation angle has begun, the X-ray diagnosis apparatus 1A of Modification 1 instructs the reconstruction circuitry 24 to reconstruct volume data and displays a generated tomosynthesis data as a tomosynthesis image. However, some radiographers may find it troublesome if a tomosynthesis image is displayed on a display device, etc. of the display 22, each time the X-ray irradiation angle changes for a predetermined rotation angle. Thus, for example, a button, etc. dedicated for receiving instructions to reconstruct volume data and to display a tomosynthesis image may be provided in the input interface 16. In other words, when the change of the X-ray irradiation angle is finished and instructions to reconstruct volume data and to display a tomosynthesis image are received at such a dedicated button, the system control circuit reconstructs volume data and displays a tomosynthesis image. Thus, it is possible to free a radiographer from being bothered by a tomosynthesis image being displayed during fluoroscopy imaging when not needed.

In the first embodiment, the system controlling circuitry 28 carries out reconstruction of volume data and the display of tomosynthesis images by associating related information, such as an X-ray irradiation angle, etc. to corresponding fluoroscopy image data, in accordance with the change of the X-ray irradiation angle; however, the first embodiment is not limited thereto. Specifically, addition of related information, reconstruction of volume data, and display of a tomosynthesis image may be performed in accordance with a relative change of a position of the X-ray tube 141 with respect to the X-ray detector 151 as a consequence of, for example, the movement of the X-ray tube arm 12 in the direction along the X-axis. The movement of the X-ray tube arm 12 in the direction along the X-axis during fluoroscopy imaging is manually controlled by the operator through the input interface 16.

Addition of related information, reconstruction of volume data, and display of a tomosynthesis image may be performed in accordance with movement of the top 13 in the direction along the X-, Y-, or Z-axis, in other words, the change of a relative position of the X-ray tube 141 with respect to the X-ray detector 151 as a consequence of each movement of the X-ray detector 151 itself. The movement of the top 13 in the direction along the X-, Y-, or Z-axis during fluoroscopy imaging may be manually controlled by the operator through the input interface 16. Furthermore, the X-ray detection unit 15 provided on the top 13 may be configured to be movable independently from the top 13 in the direction along the X-axis shown in FIG. 1, for example.

Figure 10:
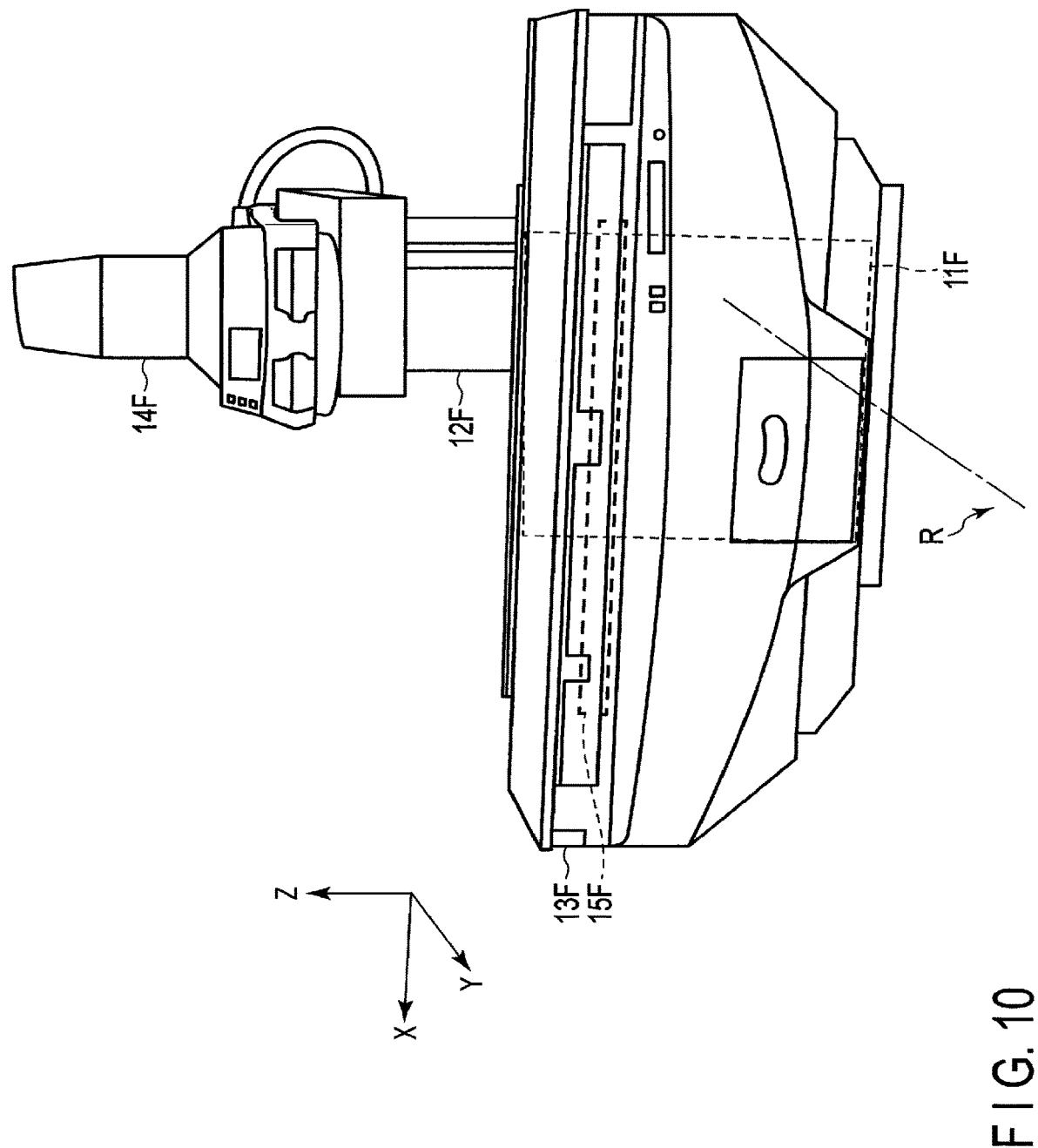
FIG. 10 is a drawing showing the outer appearance of an X-ray diagnosis apparatus according to another embodiment.

The example of the movement of the X-ray detector 151 itself is not limited to the X-ray diagnosis apparatus shown in FIG. 1. FIG. 10 is a drawing showing an example of the outer appearance of an X-ray diagnosis apparatus according to another embodiment. According to FIG. 10, the X-ray diagnosis apparatus 1F includes a support tube 11F, an X-ray tube arm 12F, a top 13F, an X-ray output unit 14F, and an X-ray detection unit 15F. The support tube 11F is connected to the X-ray tube arm 12F and the top 13F. The X-ray tube arm 12F is a holding mechanism that rotatably holds the X-ray output unit 14F in a predetermined direction. The X-ray tube arm 12F is supported by a moving mechanism of the support tube 11F in such a manner that the arm is allowed to move in a direction along the X-axis. The top 13F is supported by the moving mechanism of the support tube 11F, movably in the direction along the X-, Y-, or Z-axis. The top 13F is supported by, for example, a rotation mechanism of the support tube 11F, rotatably around the rotation central axis R. The X-ray detection unit 15F has an FPD, for example. The X-ray detection unit 15F may have a combination of I.I. and a TV camera, instead of an FPD.

At this time, the addition of related information, reconstruction of volume data, and display of a tomosynthesis image may be performed in accordance with the movement of the top 13F in the direction along the X-, Y-, or Z-axis, or the rotational movement around the rotation center axis R; in other words, the change of a relative position of the X-ray tube 141 with respect to the X-ray detector 151 as a consequence of each movement of the X-ray detection unit 15F itself.

The movement of the top 13F in the direction along the X-, Y-, or Z-axis during fluoroscopy imaging, or the rotational movement around the rotation center axis R may be manually controlled by the operator through, for example, the input interface 16.

Figure 11:
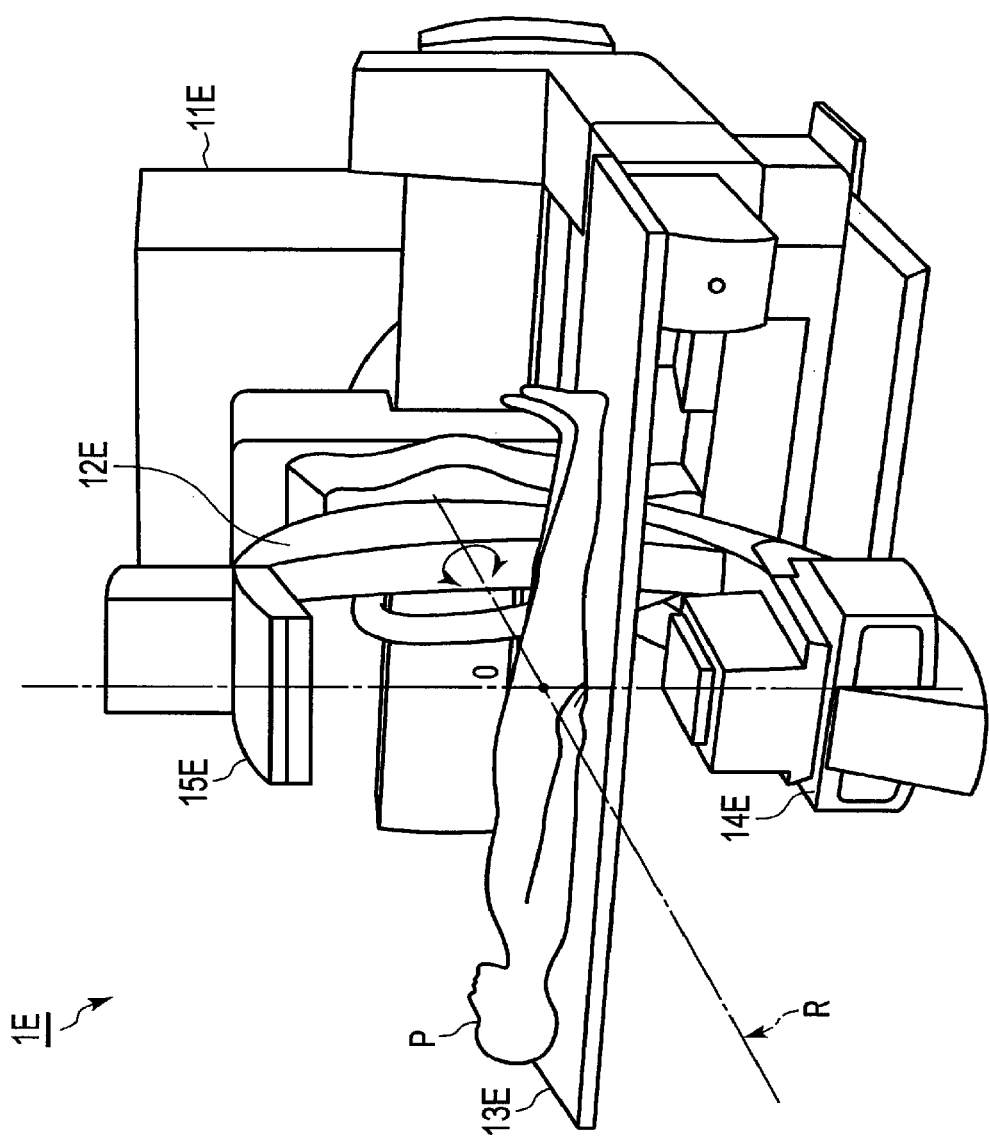
FIG. 11 is a drawing showing the outer appearance of an X-ray diagnosis apparatus according to another embodiment.

In the first embodiment, the X-ray output unit 14 is connected to the end of the X-ray tube arm 12, and the X-ray detection unit 15 is not connected to the X-ray tube arm 12 but is provided at a position facing the X-ray output unit 14; however, the configuration is not limited thereto. The X-ray tube arm 12 is a C-arm, and may be configured to be connected to an X-ray output unit at one end, and to the X-ray detection unit at the other end that faces the X-ray output unit. In this case, the C-arm 12E serves a role as a holding mechanism that rotatably holds the X-ray output unit 14E in a predetermined direction. For example, as shown in FIG. 11, the X-ray diagnosis apparatus 1E includes a support tube 11E, a C-arm 12E, a top 13 E, an X-ray output unit 14E, and an X-ray detection unit 15E. The support tube 11E is connected to the C-arm 12E and the top 13E. The C-arm 12E is supported by a moving mechanism of the support tube 11E in such a manner that the arm is allowed to move in a direction along the X-axis. The C-arm 12E is supported by, for example, a rotation mechanism of the support tube 11E, rotatably around the rotation central axis R. The top 13 E is supported by the moving mechanism of the support tube 11E, movably in the direction along the X-, Y-, or Z-axis.

The X-ray output unit 14E is provided at one end of the C-arm 12E. Of the end portions of the C-arm 12E, the X-ray detection unit 15E is provided at one end opposite to the other end where the X-ray output unit 14E is provided. The X-ray detection unit 15F has an FPD, for example. The X-ray detection unit 15F may have a combination of I.I. and a TV camera, instead of an FPD.

In the above configuration, when the C-arm 12E is rotated, the X-ray output unit 14E and the X-ray detection unit 15E are moved facing each other at all time, with the object P being interposed therebetween. In this case, the X-ray diagnosis apparatus 1E adds related information corresponding to a rotation angle to fluoroscopy image data that is output from an X-ray detector of the X-ray detection unit 15E, in accordance with the change of a rotation angle from a predetermined position of the C-arm 12E. The related information may correspond to an X-ray irradiation angle of X-rays that are output from the X-ray tube of the X-ray output unit 14E to the object P. The X-ray diagnosis apparatus 1E performs reconstruction of volume data and display of a tomosynthesis image based on a plurality of related information-added fluoroscopy image data. The rotational movement of the C-arm 12E during fluoroscopy imaging is manually controlled by the operator through the input interface 16, for example.

In the first embodiment, a tomosynthesis image based on tomosynthesis image data generated using a plurality of fluoroscopy image data generated during fluoroscopy imaging is displayed on, for example, the display 22 of the X-ray diagnosis apparatus 1; however, the configuration is not limited thereto. FIG. 12 is a block diagram showing an example of the configuration of an X-ray image diagnosis apparatus according to another embodiment. The X-ray diagnosis apparatus shown in FIG. 12 includes an X-ray diagnosis apparatus 100 and an image display apparatus 200. The X-ray diagnosis apparatus 100 and the image display apparatus 200 are connected to a local network to transmit information to a predetermined apparatus and to receive information transmitted from a predetermined apparatus. The X-ray diagnosis system may be connected to an external network, in addition to the local network or in place thereof.

The X-ray diagnosis apparatus 100 includes a communication interface 1001 in addition to the constituent elements of the X-ray diagnosis apparatus 1. The communication interface 1001 performs data communication with an external device, such as the image display apparatus 200 connected to a network, etc. shown in FIG. 12. The specification of communication with such an external device may be any specification, for example the DICOM specification.

The image display apparatus 200 includes a display circuit 2001 for displaying various images and a communication interface 2002. The communication interface 2002 performs data communication with an external device, such as the X-ray diagnosis apparatus 100 connected to the network, etc. which is shown in FIG. 12.

The X-ray diagnosis apparatus 100, during fluoroscopy imaging, for example, transmits tomosynthesis image data generated by the image processing circuitry 25 of the X-ray diagnosis apparatus 100 to the image display apparatus 200 via the communication interface circuit 1001. The image display apparatus 200 displays a tomosynthesis image based on the tomosynthesis image data received from the X-ray diagnosis apparatus 100 on the display circuit 2001.

In the first embodiment, tomosynthesis image data is generated by, for example, the image processing circuitry 25 of the X-ray diagnosis apparatus 1; however, the configuration is not limited thereto. FIG. 13 is a block diagram showing an example of the configuration of an X-ray image diagnosis apparatus according to another embodiment. The X-ray diagnosis system shown in FIG. 13 includes an X-ray diagnosis apparatus 100 and an image processing apparatus 300. The X-ray diagnosis apparatus 100 and the image processing apparatus 300 are connected to a local network, and transmit information to a predetermined apparatus, and receive information transmitted from a predetermined apparatus. The X-ray diagnosis system may be connected to an external network, in addition to the local network or in place thereof.

The X-ray diagnosis apparatus 100 includes a communication interface 1001 in addition to the constituent elements of the X-ray diagnosis apparatus 1.

The image processing apparatus 300 includes a reconstruction circuit 3001 for generating volume data, an image processing circuit 3002 for generating tomosynthesis image data image, a display circuit 3003 for displaying various images, and a communication interface 3004. The communication interface 3004 performs data communication with an external device, such as the X-ray diagnosis apparatus 100 connected to the network, etc. which is shown in FIG. 13.

The X-ray diagnosis apparatus 100 transmits, for example, a plurality of related information-added tomosynthesis image data to the image processing apparatus 300 via the communication interface circuit 1001. The reconstruction circuit 3001 of the image processing apparatus 300 reconstructs volume data based on the plurality of fluoroscopy image data received from the X-ray diagnosis apparatus 100. The image processing circuit 3002 of the image processing apparatus 300 generates tomosynthesis image data that is image data showing a desired cross-section, based on the volume data reconstructed by the reconstruction circuit 3001. Then, the display circuit 3003 of the image processing apparatus 300 displays a tomosynthesis image based on the generated tomosynthesis image data.

The term "processor" used in the above description means circuitry such as a CPU (Central Processing Unit), GPU (Graphics Processing Unit), ASIC (Application Specific Integrated Circuit), programmable logic device (e.g., an SPLD (Simple Programmable Logic Device), a CPLD (Complex Programmable Logic Device), or an FPGA (Field Programmable Gate Array)), or the like. The processor implements functions by reading programs stored in the memory and executing them. Note that it is possible to directly incorporate programs in the circuitry of the processor instead of storing them in the memory. In this case, the processor implements functions by reading programs incorporated in the circuitry and executing them. Note that each processor in this embodiment may be formed as one processor by combining a plurality of independent circuits to implement functions as well as being formed as single circuitry for each processor. Each processor of the first embodiment, Modification 1, Modification 2, and Modification 3 is not limited to a case where each processor is configured as a single circuit; a plurality of independent circuits may be combined into one processor to realize the function of the processor. Furthermore, a plurality of constituent elements shown in FIG. 2 may be integrated into one processor to realize the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnosis apparatus comprising:
an X-ray tube configured to radiate X-rays;
an input interface configured to receive an input manual operation of designating at least a direction;
a holding mechanism configured to hold the X-ray tube, and to move the X-ray tube in accordance with the input manual operation, the X-ray tube radiating X-rays during the moving;
an X-ray detector configured to detect X-rays radiated from the X-ray tube and passing through an object, the X-ray detector generating fluoroscopy image data based on the detected X-rays;
a display configured to subsequently display a fluoroscopy image based on the fluoroscopy image data;
processing circuitry configured to
associate the fluoroscopy image data with information including at least a position of the X-ray tube, the X-ray tube radiating X-rays to generate the fluoroscopy image data at the position;
reconstruct volume data by using a plurality of the fluoroscopy image data and the information associated with each of the fluoroscopy image data;
generate tomosynthesis image data based on the volume data,
monitor a position of the X-ray tube in the operation, and determine whether or not to generate the volume data based on a result of monitoring;
generate the volume data based on a result of the determination whether or not to generate the volume data; and
determine to generate the volume data when a moving amount of the X-ray tube exceeds a predetermined threshold.

2. The X-ray diagnosis apparatus according to claim 1, wherein the predetermined threshold is a moving amount of the X-ray tube necessary for generating the volume data.

3. The X-ray diagnosis apparatus according to claim 1, wherein
the input interface is further configured to receive an instruction to reconstruct volume data by the reconstruction circuitry, and
the processing circuitry is further configured to begin generating the volume data when a determination to generate the volume data is made, and the instruction is received at the input interface.

4. The X-ray diagnosis apparatus according to claim 1, wherein the processing circuitry is further configured to control the holding mechanism based on an input to the input interface and moves the X-ray tube.

5. The X-ray diagnosis apparatus according to claim 1, wherein the operation to designate at least a direction is an operation to move the X-ray tube by holding the holding mechanism by the operator.

6. The X-ray diagnosis apparatus according to claim 1, wherein the related information includes an X-ray irradiation angle of X-rays radiated from the X-ray tube to the object.

7. The X-ray diagnosis apparatus according to claim 1, wherein the related information includes a relative position of the X-ray tube with respect to the X-ray detector.

8. The X-ray diagnosis apparatus according to claim 1, wherein the related information includes an SID (source-image receptor distance) and a field of view size.

9. An X-ray diagnosis apparatus comprising:
an X-ray tube configured to radiate X-rays;
an input interface configured to receive an input manual operation of designating at least a direction;
a holding mechanism configured to hold the X-ray tube, and to move the X-ray tube in accordance with the input manual operation, the X-ray tube radiating X-rays during the moving;

an X-ray detector configured to detect X-rays radiated from the X-ray tube and passing through an object, the X-ray detector generating fluoroscopy image data based on the detected X-rays;

a display configured to subsequently display a fluoroscopy image based on the fluoroscopy image data;

processing circuitry configured to
associate the fluoroscopy image data with information including at least a position of the X-ray tube, the X-ray tube radiating X-rays to generate the fluoroscopy image data at the position;
reconstruct volume data by using a plurality of the fluoroscopy image data and the information associated with each of the fluoroscopy image data;
generate tomosynthesis image data based on the volume data,
monitor a position of the X-ray tube in the operation, and determine whether or not to generate the volume data based on a result of monitoring;
generate the volume data based on a result of the determination whether or not to generate the volume data; and
determine to generate the volume data when a position change of the X-ray tube is finished and a moving amount of the X-ray tube exceeds a predetermined threshold.

10. An X-ray diagnosis apparatus controlling method comprising:
radiating X-rays from an X-ray tube;
receiving an input manual operation to designate at least a direction;
moving the X-ray tube in accordance with the input manual operation, the X-ray tube radiating X-rays during the moving;
detecting, by an X-ray detector, X-rays radiated from the X-ray tube and that pass through an object, and generating fluoroscopy image data;
subsequently displaying a fluoroscopy image based on the fluoroscopy image data;
associating the fluoroscopy image data with information including at least a position of the X-ray tube, the X-ray tube radiating X-rays to generate the fluoroscopy image data at the position;
reconstructing volume data using a plurality of the fluoroscopy image data and the information associated with each of the fluoroscopy image data;

generating tomosynthesis image data based upon the volume data;
monitoring a position of the X-ray tube in the operation, and determine whether or not to generate the volume data based on a result of monitoring;
generating the volume data based on a result of the determination; and
generating the volume data when a moving amount of the X-ray tube exceeds a predetermined threshold.

11. An X-ray diagnosis system comprising an X-ray diagnosis apparatus and an image processing apparatus, the X-ray diagnosis apparatus comprising:
an X-ray tube configured to radiate X-rays;
an input interface configured to receive an input manual operation of designating at least a direction;
a holding mechanism configured to the X-ray tube, and to move the X-ray tube in accordance with the input manual operation, the X-ray tube radiating X-rays during the moving;
an X-ray detector configured to X-rays radiated from the X-ray tube and passing through an object, the X-ray detector generating fluoroscopy image data based on the detected X-rays;
a display configured to subsequently display a fluoroscopy image based on the fluoroscopy image data; and
processing circuitry configured to associate the fluoroscopy image data with information including at least a position of the X-ray tube, the X-ray tube radiating X-rays to generate the fluoroscopy image data at the position; and
the image processing apparatus comprising processing circuitry configured to:
reconstruct volume data by using a plurality of the fluoroscopy image data and the information associated with each of the fluoroscopy image data;
generate tomosynthesis image data based upon the volume data;
monitor a position of the X-ray tube in the operation, and determine whether or not to generate the volume data based on a result of monitoring;
generate the volume data based on a result of the determination whether or not to generate the volume data; and
determine to generate the volume data when a moving amount of the X-ray tube exceeds a predetermined threshold.

* * * * *